(12) United States Patent
Jagerovic et al.

(10) Patent No.: US 8,349,878 B2
(45) Date of Patent: Jan. 8, 2013

(54) 1,2,4-TRIAZOLE DERIVATIVES AS SIGMA RECEPTOR INHIBITORS

(75) Inventors: Nadine Jagerovic, Madrid (ES); Jose Maria Cumella-Montanchez, Madrid (ES); Maria Pilar Goya-Laza, Madrid (ES); Alberto Dordal Zueras, Barcelona (ES); Maria Rosa Cuberes-Altisent, Barcelona (ES)

(73) Assignee: Laboratorios del Dr. Esteve, S.A., Barcelona (ES)

( * ) Notice: Subject to any disclaimer, the term of this patent is extended or adjusted under 35 U.S.C. 154(b) by 0 days.

(21) Appl. No.: 13/229,917

(22) Filed: Sep. 12, 2011

(65) Prior Publication Data

US 2012/0004211 A1    Jan. 5, 2012

Related U.S. Application Data

(62) Division of application No. 12/514,202, filed as application No. PCT/EP2007/062006 on Nov. 7, 2007, now Pat. No. 8,039,497.

(30) Foreign Application Priority Data

Nov. 10, 2006   (EP) ..................................... 06380291

(51) Int. Cl.
*A61K 31/44*   (2006.01)
*C07D 249/00*   (2006.01)

(52) U.S. Cl. ..................................... 514/363; 548/262.2
(58) Field of Classification Search .................. 514/363; 548/262.2

See application file for complete search history.

(56) References Cited

U.S. PATENT DOCUMENTS 3,632,345 A * 1/1972 Marx et al. .................... 430/543
6,638,954 B2 10/2003 Kadaba

FOREIGN PATENT DOCUMENTS

| WO | 9109594 | A1 | 7/1991 |
| WO | 0236119 | A1 | 5/2002 |
| WO | 03092681 | A1 | 11/2003 |
| WO | 2004096781 | A1 | 11/2004 |
| WO | 2005039550 | A2 | 5/2005 |
| WO | 2005039569 | A1 | 5/2005 |
| WO | 2006092731 | A1 | 9/2006 |

OTHER PUBLICATIONS

Maurice, et al., Brain Research Review, vol. 37, 2001, pp. 116-132.*
Walker, J.M. et al., "Sigma Receptors: Biology and Function", Pharmacological Reviews, 1990, 42, 355.
Snyder, S.H., et al., "Receptor Mechanisms in Antipsychotic Drug Action: Focus on Sigma Receptors", Journal of Neuropsychiatry, 1989, 1, 7.
Quirion, R. et al. "A proposal for the classification of sigma binding sites", Trends Pharmacol. Sci, 1992, 13:85-86.
Hanner, M. et al., "Purification, molecular cloning, and expression of the mammalian sigmal-bindng site", Proc. Natl. Acad. Sci., 1996, 93:8072-8077.
Czollner, L. et al., "A Facile Synthesis of 1,5-Diphenyl-3-(substituted oxy)-1H-1,2,4-triazoles", Arch. Pharm. 1990, 323 (4), 221-223.
DeHaven-Hudkins, D.L. et al., "Characterization of the binding of [3H](+)-pentazocine to σ recognition sites in guinea pig brain", Eur. J. Pharmacol.; 1992, 227, 371-378.
Lowry, O.H., et al., Protein Measurement With the Folin Phenol Reagent, J. Biol. Chem, 1951, 193, 265.
Maliszewska-Guz, A. et al., "Derivatives of hydroxy-1,2,4,-triazole. Part III. Reaction of hydroxy-1,2,4-triazoles with ethylene chlorohydrin", Annales Universitatis Mariae Curie-Sklodowska, Sectio AA: Chemia 1995, vol. Date 1991-1992, 46-47, 35-40 (abstract in English).
SciFinder search results.
International Search Report for PCT/EP2007/062006, dated Mar. 17, 2008.

* cited by examiner

*Primary Examiner* — Susannah Chung
(74) *Attorney, Agent, or Firm* — Hoffmann & Baron, LLP

(57) ABSTRACT

The invention relates to the use of compounds having pharmacological activity towards the sigma receptor, and more particularly to 1,2,4-triazole derivatives of formula I

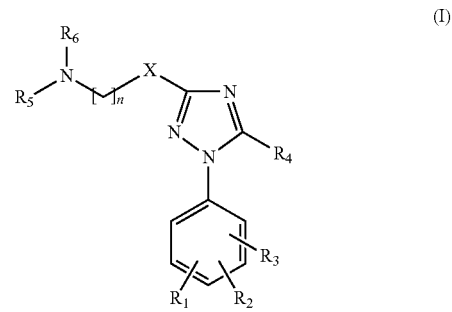

to processes of preparation of such compounds and to pharmaceutical compositions comprising them.

16 Claims, No Drawings

1,2,4-TRIAZOLE DERIVATIVES AS SIGMA RECEPTOR INHIBITORS

CROSS-REFERENCE TO RELATED APPLICATIONS

This application is a Divisional application of Ser. No. 12/514,202, filed May 8, 2009, which claims the benefit to International Application No. PCT/EP2007/062006, filed Nov. 7, 2007, which claims the benefit to European Application No. 06380291.2, filed Nov. 10, 2006, the contents of which are incorporated by reference herein.

FIELD OF THE INVENTION

The present invention relates to the use of compounds having pharmacological activity towards the sigma receptor, and more particularly to some 1,2,4-triazole derivatives, to processes of preparation of such compounds and to pharmaceutical compositions comprising them.

BACKGROUND OF THE INVENTION

The search for new therapeutic agents has been greatly aided in recent years by better understanding of the structure of proteins and other biomolecules associated with target diseases. One important class of these proteins is the sigma (σ) receptor, a cell surface receptor of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, *Pharmacological Reviews*, 1990, 42, 355). It has been reported that the known sigma receptor ligand rimcazole clinically shows effects in the treatment of psycosis (Snyder, S. H., Largent, B. L. J. Neuropsychiatry 1989, 1, 7). The sigma binding sites have preferential affinity for the dextrorotatory isomers of certain opiate benzomorphans, such as (+)SKF 10047, (+)cyclazocine, and (+)pentazocine and also for some narcoleptics such as haloperidol.

The sigma receptor has at least two subtypes, which may be discriminated by stereoselective isomers of these pharmacoactive drugs. SKF 10047 has nanomolar affinity for the sigma 1 (σ-1) site, and has micromolar affinity for the sigma (σ-2) site. Haloperidol has similar affinities for both subtypes. Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. *Trends Pharmacol. Sci.*, 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. *Proc. Natl. Acad. Sci.*, 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find selective ligands. Thus, the prior art discloses different sigma receptor ligands.

International Patent Application No WO 91/09594 generically describes a broad class of sigma receptor ligands some of which are 4-phenylpiperidine, -tetrahydro-pyridine or -piperazine compounds having an optionally substituted aryl or heteroaryl, alkyl, alkenyl, alkynyl, alkoxy or alkoxyalkyl substituent on the ring N-atom.

With regard to the chemical structure of the compounds described in the present patent application, it is to be highlighted that the 1,2,4-triazole ring system has been the subject of considerable research mainly due to the pharmacological properties shown by some of its derivatives and also because of its usefulness in synthetic organic chemistry. Recent reports have dealt with 1,2,4-triazoles derivatives as oxytocin antagonists (WO2006/092731) and also as inhibitors of MPO enzyme (WO2004/096781). 1,2,4-triazoles have also been described as useful agents in the treatment of psychiatric disorders due to their CB1-receptor activity (WO2005/039550), for the treatment of autoimmune diseases, such as sclerosis or arthritis rumatoide (WO03/092681) and also for the prevention of urological disorders since they act as GABAb agonists (WO2005/039569). In addition, some 3-hydroxyalkyl-1,5-diaryl-[1,2,4-triazoles] have shown a significant anti-inflammatory activity (Archiv. Der Pharmazie, 1990, 323(4), 221-223).

However, none of these documents suggests the effect of these compounds on the sigma receptor.

There is still a need to find compounds that have pharmacological activity towards the sigma receptor, being both effective and selective, and having good "drugability" properties, i.e. good pharmaceutical properties related to administration, distribution, metabolism and excretion.

SUMMARY OF THE INVENTION

We have now found a family of structurally distinct triazole derivatives which are particularly selective inhibitors of the sigma-1 receptor. The compounds of the invention present a 1,2,4-triazole group which are characterized by the substitution in the 3 position of an alkyl chain which ends in an amine type substituent.

In one aspect the invention is directed to the use of a compound of the formula (I):

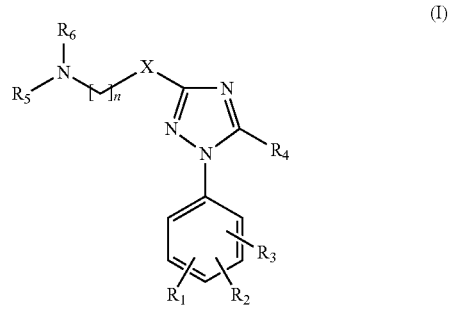

wherein:
$R_1$, $R_2$ and $R_3$ are independently selected from hydrogen, halogen, hydroxyl, alcoxyl, substituted or unsubstituted $C_1$-$C_6$ alkyl, cyano, $NR^aR^b$, $NHCONR^c$, $NHSO_2R^d$, COOH, $COOR^e$, wherein $R^a$ is hydrogen or $C_1$-$C_6$ alkyl and $R^b$, $R^c$, $R^d$ and $R^e$ are independently a $C_1$-$C_6$ alkyl;
$R_4$ is selected from hydrogen, $C_1$-$C_6$ alkyl, cycloalkyl, heterocyclyl and heteroaryl;

$R_5$ and $R_6$ are independently a $C_1$-$C_6$ alkyl or form, together with the nitrogen atom to which they are attached, a substituted or unsubstituted heterocyclyl group;

X is selected from —S—, —SO—, —SO$_2$— and O; and n is an integer selected from 1, 2, 3, 4, 5, 6, 7 and 8, or a pharmaceutically acceptable salt, isomer, prodrug or solvate thereof, in the manufacture of a medicament for the treatment or prophylaxis of a sigma-1 receptor mediated disease or condition.

In a particular embodiment, the compound of formula (I) is used in the manufacture of a medicament for the treatment of diarrhoea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer, psychotic conditions, in particular depression, anxiety or schizophrenia; inflammation or autoimmune diseases.

In a more preferred embodiment the medicament is for the treatment of pain, especially neuropathic pain, inflammatory pain or other pain conditions involving allodynia and/or hyperalgesia.

In another particular embodiment the compound of formula (I) is use as pharmacological tool, as anxiolytic or as immunosuppressant.

Another aspect of the invention relates to a compound of formula (I) as defined above for its use in the treatment of a sigma-1 receptor mediated disease or condition.

In a second aspect the invention is directed to a compound of formula (I):

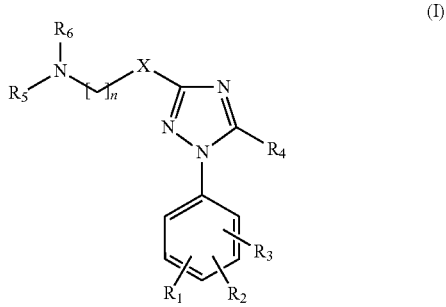

wherein:

$R_1$, $R_2$ and $R_3$ are independently selected from hydrogen, halogen, hydroxyl, $C_1$-$C_6$ alcoxyl, substituted or unsubstituted $C_1$-$C_6$ alkyl, cyano, $NR^aR^b$, $NHCONR^c$, $NHSO_2R^d$, COOH, COOR$^e$, wherein R$^a$ is hydrogen or $C_1$-$C_6$ alkyl and R$^b$, R$^c$, R$^d$ and R$^e$ are independently a $C_1$-$C_6$ alkyl;

$R_4$ is selected from hydrogen, $C_1$-$C_6$ alkyl, cycloalkyl, heteroaryl and heterocyclyl;

$R_5$ and $R_6$ are independently a $C_1$-$C_6$ alkyl or form, together with the nitrogen atom to which they are attached, a substituted or unsubstituted heterocyclyl group;

X is selected from —S—, —SO—, —SO$_2$— and O; and n is an integer selected from 1, 2, 3, 4, 5, 6, 7 and 8, or a pharmaceutically acceptable salt, isomer, prodrug or solvate thereof, with the proviso that $R_4$ is not cyclopropyl; and when $R_4$ is hydrogen at least one of $R_1$, $R_2$ and $R_3$ is not hydrogen.

In a preferred embodiment, at least one of $R_1$ to $R_3$ is hydrogen. In another preferred embodiment, two of $R_1$ to $R_3$ are hydrogen or halogen, the last being preferably chloride.

In another embodiment, $R_4$ is preferably a $C_1$-$C_6$ alkyl, more preferably is methyl.

In one embodiment $R_5$ and $R_6$ are independently a $C_1$-$C_6$ alkyl, more preferably ethyl or isopropyl.

In another embodiment $R_5$ and $R_6$ form, together with the nitrogen to which they are attached, a substituted or unsubstituted heterocyclyl group, preferably selected from pyrrolidine, piperidine, azepane and morpholine.

Further, in a preferred embodiment n is 1, 2, 3, 4 or 5.

In a third aspect, the invention is directed to a process for the preparation of a compound of formula (I) or a salt, isomer, prodrug or solvate thereof which comprises the alkylation of the corresponding 5-alkyl-1-aryl-1H-1,2,4-triazol-3-thiol/ol of formula (II) with an alkylating agent.

In another aspect, the invention relates to a process for the preparation of a compound of formula (I) or a salt, isomer, prodrug or solvate thereof which comprises the reaction of the compound of formula (V) with an amine NHR$_5$R$_6$, wherein $R_5$ and $R_6$ are independently a $C_1$-$C_6$ alkyl or form, together with the nitrogen atom to which they are attached, a substituted or unsubstituted heterocyclyl group.

In another aspect, the invention is directed to the intermediate compound of formula (V).

Finally, in another aspect the invention is directed to a pharmaceutical composition which comprises a compound as defined above or a pharmaceutically acceptable salt, isomer, prodrug or solvate thereof, and a pharmaceutically acceptable carrier, adjuvant or vehicle.

The above mentioned preferences and embodiments can be combined to give further preferred compounds or uses.

DETAILED DESCRIPTION OF THE INVENTION

The typical compounds of this invention effectively and selectively inhibit the sigma-1 receptor.

In the present description the following terms have the meaning indicated:

"$C_1$-$C_6$ alkyl" refers to a straight or branched hydrocarbon chain radical consisting of carbon and hydrogen atoms, containing no unsaturation, having one to six carbon atoms, and which is attached to the rest of the molecule by a single bond, e.g., methyl, ethyl, propyl, isopropyl, n-butyl, tert-butyl, isobutyl, n-pentyl, n-hexyl, etc.

"$C_1$-$C_6$ alcoxyl" refers to a radical of the formula OR wherein R is a $C_1$-$C_6$ alkyl radical as defined above, e.g., methoxy, ethoxy, propoxy, etc.

"Cycloalkyl" refers to stable 3- to 10-membered monocyclic or bicyclic radical which is fully saturated, and which consists solely of carbon and hydrogen atoms, such as cyclopentyl, cyclohexyl, etc. Unless otherwise stated specifically in the specification, the term "cycloalkyl" is meant to include cycloalkyl radicals which are optionally substituted by one or more substituents such as alkyl, halogen, hydroxyl, amino, cyano, nitro, alkoxyl, barboxyl, alcoxycarbonyl, etc.

"Heteroaryl" refers to a substituted or unsubstituted stable 3- to 8-membered ring radical which is partially unsaturated or aromatic and which consists of carbon atoms and from one to three heteroatoms selected from the group consisting of nitrogen, oxygen and sulfur, preferably a 4- to 7-membered ring with one or more heteroatoms, more preferably a 5, 6 or 7-membered ring with one or more heteroatoms, provided that at least one of the heteroatoms are nitrogen. Additionally, the heteroaryl may be also monocyclic, bicyclic or tricyclic ring system, which may include fused ring systems. Examples of such heteroaryls include, but are not limited to benzimidazole, benzothiazole, isothiazole, imidazole, indole, purine, quinoline, thiadiazole, pyrrole, pyrazole, oxazole, isoxazole, triazole, imidazole, etc.

"Heterocyclyl" refers to a substituted or unsubstituted stable 3- to 8-membered ring radical which is fully saturated and which consists of carbon atoms and from one to three heteroatoms selected from the group consisting of nitrogen, oxygen and sulfur, preferably a 4- to 7-membered ring with one or more heteroatoms, more preferably a 5, 6 or 7-membered ring with one or more heteroatoms, provided that at least one of the heteroatoms are nitrogen. Additionally, the heterocycle may be also monocyclic, bicyclic or tricyclic ring system, which may include fused ring systems; and the nitrogen, carbon or sulfur atoms in the heterocyclyl radical may be optionally oxidised; the nitrogen atom may be optionally quaternized. Examples of such heterocycles include, but are not limited to azepine, piperidine, piperazine, morpholine, etc.

The heterocyclyl and heteroaryl groups may be substituted at one or more available positions by one or more suitable groups, e.g., halogen such as fluoro, chloro, bromo and iodo; cyano; hydroxyl; nitro; alkyl groups including those groups having 1 to about 12 carbon atoms or from 1 to about 6 carbon atoms and more preferably 1-3 carbon atoms; carbocyclic aryl having 6 or more carbons, particularly phenyl or naphthyl and aralkyl such as benzyl. Unless otherwise indicated, an optionally substituted group may have a substituent at each substitutable position of the group, and each substitution is independent of the other.

"Halogen" refers to bromo, chloro, iodo or fluoro.

The 1,2,4-triazole derivatives used in the present invention are distinguished by a broad spectrum of beneficial effects, while at the same time showing relatively little undesired effects, i.e., effects which do not positively contribute to or even interfere with the well being of the patient.

Thus, one aspect of this invention relates to a method of treating or preventing a sigma-1 receptor mediated disease which method comprises administering to a patient in need of such a treatment a therapeutically effective amount of a compound of formula I or a pharmaceutical composition thereof. Among the sigma-1 mediated diseases that can be treated or prevented are diarrhoea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer, psychotic conditions, in particular depression, anxiety or schizophrenia; inflammation, autoimmune diseases, especially neuropathic pain, inflammatory pain or other pain conditions involving allodynia and/or hyperalgesia. The compounds of the invention can also be employed as pharmacological tool or as anxiolytic or immunosuppressant.

In one embodiment of the invention, it is preferred that in the compound of formula (I) used in the present invention, at least one of $R_1$ to $R_3$ is hydrogen. In another embodiment, it is preferred that two of $R_1$ to $R_3$ are hydrogen or halogen, the last being preferably chloride.

In another embodiment, $R_4$ is preferably a lower alkyl, more preferably is methyl.

In one embodiment $R_5$ and $R_6$ are independently a lower alkyl, more preferably ethyl or isopropyl.

In another embodiment $R_5$ and $R_6$ form, together with the nitrogen to which they are attached, a substituted or unsubstituted heterocyclyl group, preferably selected from pyrrolidine, piperidine, azepane and morpholine.

Further, in a preferred embodiment n is 1, 2, 3, 4 or 5.

Preferred compounds of formula I are the following:
4-[2-(3,4-dichlorophenyl)-5-methyl-1H-1,2,4-triazole-3-ylthio ethyl]morpholine;
1-[2-(3,4-dichlorophenyl)-5-methyl-1H-1,2,4-triazole-3-yl-thioethyl]piperidine;
1-[2-(3,4-dichlorophenyl)-5-methyl-1H-1,2,4-triazole-3-yl-thio ethyl]pyrrolidine;
2-[2-(3,4-dichlorophenyl)-5-methyl-1H-1,2,4-triazole-3-yl-thio]-N,N-diisopropyl ethanamine;
2-[1-(3,4-dichlorophenyl)-5-methyl-1H-1,2,4-triazole-3-yl-thio]-N,N-diethyl ethanamine;
1-[2-(1-(3,4-dichlorophenyl)-5-methyl-1H-1,2,4-triazol-3-yl-thio)ethyl]azepane;
4-[3-(1-(3,4-dichlorophenyl)-5-methyl-1H-1,2,4-triazol-3-ylthio)propyl]morpholine;
1-[3-(1-(3,4-dichlorophenyl)-5-methyl-1H-1,2,4-triazol-3-yl-thio)propyl]-4-pyrrolidine;
1-[3-(1-(3,4-dichlorophenyl)-5-methyl-1H-1,2,4-triazol-3-ylthio)propyl]-4-phenylpiperidine;
1-[4-(1-(3,4-dichlorophenyl)-5-methyl-1H-1,2,4-triazol-3-yl-thio)butyl]-4-phenylpiperidine;
4-[4-(1-(3,4-dichlorophenyl)-5-methyl-1H-1,2,4-triazol-3-yl-thio)butyl]morpholine;
1-[5-(1-(3,4-dichlorophenyl)-5-methyl-1H-1,2,4-triazol-3-ylthio)pentyl]piperidine;
4-[5-(1-(3,4-dichlorophenyl)-5-methyl-1H-1,2,4-triazol-3-ylthio)pentyl]morpholine;
1-[5-(1-(3,4-dichlorophenyl)-5-methyl-1H-1,2,4-triazol-3-ylthio)pentyl]pyrrolidine;
1-[2-(1-(3,4-dichlorophenyl)-5-methyl-1H-1,2,4-triazol-3-yl-sulfinyl)ethyl]pyrrolidine;
4-[2-(1-(3,4-dichlorophenyl)-5-methyl-1H-1,2,4-triazol-3-yl-sulfinyl)-ethyl]-morpholine;
2-[2-(1-(3,4-dichlorophenyl)-5-methyl-1H-1,2,4-triazol-3-ylsulfinyl]-N,N-diisopropylethanamine;
1-[4-(1-(3,4-dichlorophenyl)-5-methyl-1H-1,2,4-triazol-3-ylsulfinyl)butyl]-4-phenylpiperidine;
1-[2-(3,4-dichlorophenyl)-5-methyl-1H-1,2,4-triazol-3-yl-sulfonyl]ethyl pyrrolidine;
2-[1-(3,4-dichlorophenyl)-5-methyl-1H-1,2,4-triazol-3-yl-sulfonyl]-N,N-diethylethanamine;
4-[4-(1-(3,4-dichlorophenyl)-5-methyl-1H-1,2,4-triazol-3-yl-sulfonyl)-butyl]morpholine;
1-[2-(3,4-dichlorophenyl)-5-methyl-1H-1,2,4-triazol-3-yloxy)ethyl]piperidine;
2-[1-(3,4-dichlorophenyl)-5-methyl-1H-1,2,4-triazol-3-yloxy]-N,N-diethylethanamine;
1-[2-(1-(3,4-dichlorophenyl)-5-methyl-1H-1,2,4-triazol-3-yloxy)ethyl]pyrrolidine;
4-[2-(1-(3,4-dichlorophenyl)-5-methyl-1H-1,2,4-triazol-3-yloxy)ethyl]morpholine;
2-(5-methyl-1-phenyl-1H-1,2,4-triazol-3-yloxy)-N,N-diethyl ethanamine;
1-[2-(5-methyl-1-phenyl-1H-1,2,4-triazol-3-yloxy)ethyl]pyrrolidine;
4-[2-(5-methyl-1-phenyl-1H-1,2,4-triazol-3-yloxy)ethyl]morpholine;
1-[2-(5-methyl-1-phenyl-1H-1,2,4-triazol-3-yloxy)ethyl]piperidine;
4-[4-(5-methyl-1-phenyl-1H-1,2,4-triazol-3-yloxy)butyl]morpholine;

1-[2-(1-(3,4-dichlorophenyl)-5-methyl-1H-1,2,4-triazol-3-ylthio)ethyl]-4-methylpiperidine;
4-[2-(5-methyl-1-phenyl-1H-1,2,4-triazol-3-ylthio)ethyl]morpholine;
4-[2-(1-(4-chlorophenyl)-5-methyl-1H-1,2,4-triazol-3-ylthio)ethyl]morpholine;
N-[2-(1-(3-chlorophenyl)-5-methyl-1H-1,2,4-triazol-3-ylthio)ethyl]-N,N-diisopropylpropan-2-amine;
1-[2-(1-(3-chlorophenyl)-5-methyl-1H-1,2,4-triazol-3-ylthio)ethyl]piperidine;
4-[2-(1-(3-chlorophenyl)-5-methyl-1H-1,2,4-triazol-3-ylthio)ethyl]morpholine;
4-[2-(1-(3-chlorophenyl)-5-methyl-1H-1,2,4-triazol-3-ylthio)ethyl]pyrrolidine;
2-[1-(3-chlorophenyl)-5-methyl-1H-1,2,4-triazol-3-ylthio]-N,N-diethylethanamine;
4-[1-(3,4-dichlorophenyl)-5-methyl-1H-1,2,4-triazol-3-ylthio]-N,N-diethylbutan-1-amine;
1-[4-(1-(3,4-dichlorophenyl)-5-methyl-1H-1,2,4-triazol-3-ylthio)butyl]piperidine;
1-[4-(1-(3,4-dichlorophenyl)-5-methyl-1H-1,2,4-triazol-3-ylthio)butyl]pyrrolidine;
2-[1-(3,4-dichlorophenyl)-5-methyl-1H-1,2,4-triazol-3-ylsulfinyl]-N,N-diethylethanamine;
1-[2-(1-(3-chlorophenyl)-5-methyl-1H-1,2,4-triazol-3-ylsulfinyl)ethyl]pyrrolidine
1-[2-(1-(3-chlorophenyl)-5-methyl-1H-1,2,4-triazol-3-ylsulfinyl)ethyl]morpholine
1-[2-(1-(3-chlorophenyl)-5-methyl-1H-1,2,4-triazol-3-ylsulfinyl)ethyl]-N,N-diethylamine;
1-[2-(1-(3-chlorophenyl)-5-methyl-1H-1,2,4-triazol-3-ylsulfonyl)ethyl]pyrrolidine
1-[2-(1-(3-chlorophenyl)-5-methyl-1H-1,2,4-triazol-3-ylsulfonyl)ethyl]-N,N-diisopropilamine;
1-[2-(1-(3-chlorophenyl)-5-methyl-1H-1,2,4-triazol-3-ylsulfonyl)ethyl]-N,N-diethylamine;
or a pharmaceutically acceptable salt, isomer, prodrug or solvate thereof.

Additionally, in another preferred embodiment of the invention the compound of formula I is an oxalic salt thereof.

Preferred salts of the compounds of formula I are the following:
4-[2-(3,4-dichlorophenyl)-5-methyl-1H-1,2,4-triazole-3-ylthio ethyl]morpholine oxalate;
1-[2-(3,4-dichlorophenyl)-5-methyl-1H-1.2.4-triazole-3-ylthio)ethyl]piperidine oxalate;
1-[2-(3,4-dichlorophenyl)-5-methyl-1H-1,2,4-triazole-3-ylthio ethyl]pyrrolidine oxalate;
2-[2-(3,4-dichlorophenyl)-5-methyl-1H-1,2,4-triazole-3-ylthio]-N,N-diisopropyl ethanamine oxalate;
2-[1-(3,4-dichlorophenyl)-5-methyl-1H-1,2,4-triazole-3-ylthio]-N,N-diethyl ethanamine oxalate;
1-[2-(1-(3,4-dichlorophenyl)-5-methyl-1H-1,2,4-triazol-3-yl-thio)ethyl]azepane oxalate;
4-[3-(1-(3,4-dichlorophenyl)-5-methyl-1H-1,2,4-triazol-3-ylthio)propyl]morpholine oxalate;
1-[3-(1-(3,4-dichlorophenyl)-5-methyl-1H-1,2,4-triazol-3-yl-thio)propyl]pyrrolidine oxalate;
1-[3-(1-(3,4-dichlorophenyl)-5-methyl-1H-1,2,4-triazol-3-ylthio)propyl]-4-phenylpiperidine oxalate;
1-[4-(1-(3,4-dichlorophenyl)-5-methyl-1H-1,2,4-triazol-3-yl-thio)butyl]-4-phenylpiperidine oxalate;
4-[4-(1-(3,4-dichlorophenyl)-5-methyl-1H-1,2,4-triazol-3-yl-thio)butyl]morpholine oxalate;
1-[5-(1-(3,4-dichlorophenyl)-5-methyl-1H-1,2,4-triazol-3-ylthio)pentyl]piperidine oxalate;
4-[5-(1-(3,4-dichlorophenyl)-5-methyl-1H-1,2,4-triazol-3-ylthio)pentyl]morpholine oxalate;
1-[5-(1-(3,4-dichlorophenyl)-5-methyl-1H-1,2,4-triazol-3-ylthio)pentyl]pyrrolidine oxalate;
4-[2-(1-(3,4-dichlorophenyl)-5-methyl-1H-1,2,4-triazol-3-yloxy)ethyl]morpholine oxalate;
4-[2-(3,4-dichlorophenyl)-5-methyl-1H-1,2,4-triazole-3-ylthio)ethyl]morpholine hydrochloride;
1-[2-(1-(3,4-dichlorophenyl)-5-methyl-1H-1,2,4-triazol-3-ylthio)ethyl]-4-methyl piperidinium oxalate;
4-[2-(5-methyl-1-phenyl-1H-1,2,4-triazol-3-ylthio)ethyl]morpholinium oxalate;
4-[2-(1-(4-chlorophenyl)-5-methyl-1H-1,2,4-triazol-3-ylthio)ethyl]morpholinium oxalate;
N-[2-(1-(3-chlorophenyl)-5-methyl-1H-1,2,4-triazol-3-ylthio)ethyl]-N,N-diisopropylpropan-2-aminium oxalate;
1-[2-(1-(3-chlorophenyl)-5-methyl-1H-1,2,4-triazol-3-ylthio)ethyl]piperidinium oxalate;
4-[2-(1-(3-chlorophenyl)-5-methyl-1H-1,2,4-triazol-3-ylthio)ethyl]morpholinium oxalate;
4-[2-(1-(3-chlorophenyl)-5-methyl-1H-1,2,4-triazol-3-ylthio)ethyl]pyrrolidinium oxalate;
2-[1-(3-chlorophenyl)-5-methyl-1H-1,2,4-triazol-3-ylthio]-N,N-diethylethan aminium oxalate.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon or $^{15}$N-enriched nitrogen are within the scope of this invention.

The term "pharmaceutically acceptable salts, isomers, solvates, prodrugs" refers to any pharmaceutically acceptable salt, isomer, solvate, prodrug or any other compound which, upon administration to the recipient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, isomers, solvates, prodrugs and derivatives can be carried out by methods known in the art.

For instance, pharmaceutically acceptable salts of compounds provided herein are synthesized from the parent compound which contains a basic moiety by conventional chemical methods. Generally, such salts are, for example, prepared by reacting the free base forms of these compounds with a stoichiometric amount of the appropriate acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate.

Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Any compound that is a prodrug of a compound of formula I is within the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides.

The compounds of the invention may be in crystalline form either as free compounds or as solvates and it is intended that both forms are within the scope of the present invention. Methods of solvation are generally known within the art. Suitable solvates are pharmaceutically acceptable solvates. In a particular embodiment the solvate is a hydrate.

The compounds of formula I, their salts, isomers, prodrugs or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula I, or of its salts, isomers, solvates or prodrugs.

The compounds of the present invention represented by the above described formula I may include enantiomers depending on the presence of chiral centres. The single isomers, enantiomers or diastereoisomers and mixtures thereof fall within the scope of the present invention.

The compounds of formula (I) defined above can be obtained by available synthetic procedures. For example, compounds of formula (I) can be prepared by alkylation of the corresponding 5-alkyl-1-aryl-1H-1,2,4-triazol-3-thiol/ol of formula (II):

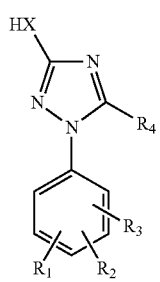

(II)

with an alkylating agent,
wherein:
$R_1$, $R_2$ and $R_3$ are independently selected from hydrogen, halogen, hydroxyl, alcoxyl, substituted or unsubstituted $C_1$-$C_6$ alkyl, cyano, $NR^aR^b$, $NHCONR^c$, $NHSO_2R^d$, COOH, $COOR^e$, wherein $R^a$ is hydrogen or $C_1$-$C_6$ alkyl and $R^b$, $R^c$, $R^d$ and $R^e$ are independently a $C_1$-$C_6$ alkyl;
$R_4$ is selected from hydrogen, $C_1$-$C_6$ alkyl, cycloalkyl, heterocyclyl and heteroaryl; and
X is O or S,
with the proviso that:
$R_4$ is not cyclopropyl; and
when $R_4$ is hydrogen at least one of $R_1$, $R_2$ and $R_3$ is not hydrogen.

This alkylating reaction preferably takes place in the presence of a base, such as for example a carbonate, and using a protic solvent such as a lower alcohol, for example methanol.

The compound 5-alkyl-1-aryl-1H-1,2,4-triazole-3-thiol/ol of formula (II) can be obtained by cycloaddition of semicarbazides according to the procedure published in *Arch. Pharm.* (1990), 323, 221-223.

In a particular embodiment of the invention, the alkylating agent is a compound of formula (III):

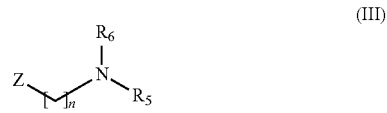

(III)

wherein
Z is a halogen,
$R_5$ and $R_6$ are independently a $C_1$-$C_6$ alkyl or form, together with the nitrogen atom to which they are attached, a substituted or unsubstituted heterocyclyl group, and
n is selected form 1, 2, 3, 4, 5, 6, 7 and 8.

In another embodiment of the invention, the alkylating agent is a compound of formula (IV):

(IV)

wherein Z and n are as defined above.

In this last case, an additional step is required to obtain the compound of formula (I) in which the compound obtained after the alkylation reaction is reacted with an amine $NHR_5R_6$, wherein $R_5$ and $R_6$ are as defined above.

Accordingly, compounds of formula (I) can also be prepared by a process which comprises the reaction of the compound of formula (V):

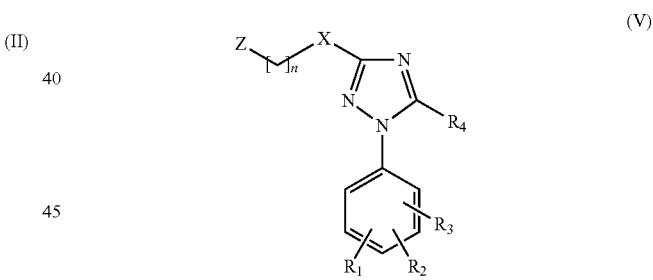

(V)

wherein:
$R_1$, $R_2$ and $R_3$ are independently selected from hydrogen, halogen, hydroxyl, alcoxyl, substituted or unsubstituted $C_1$-$C_6$ alkyl, cyano, $NR^aR^b$, $NHCONR^c$, $NHSO_2R^d$, COOH, $COOR^e$, wherein $R^a$ is hydrogen or $C_1$-$C_6$ alkyl and $R^b$, $R^c$, $R^d$ and $R^e$ are independently a $C_1$-$C_6$ alkyl;
$R_4$ is selected from hydrogen, $C_1$-$C_6$ alkyl, cycloalkyl, heterocyclyl and heteroaryl;
X is O or S.
Z is a halogen;
n selected form 1, 2, 3, 4, 5, 6, 7 and 8,
with the proviso that:
$R_4$ is not cyclopropyl; and
when $R_4$ is hydrogen at least one of $R_1$, $R_2$ and $R_3$ is not hydrogen,
with an amine $NHR_5R_6$, wherein $R_5$ and $R_6$ are independently a $C_1$-$C_6$ alkyl or form, together with the nitrogen atom to which they are attached, a substituted or unsubstituted heterocyclyl group.

Compounds of formula (I) wherein X is —SO— or —SO$_2$— can be obtained by oxidation of the corresponding 3-(alkylthio)-1H-1,2,4-triazole prepared according to any of the reactions described above, by methods known by a skilled person. For example, the oxidation reaction can be carried using Oxone® as oxidizing agent.

In another embodiment, the invention relates to the intermediate compound of formula (V):

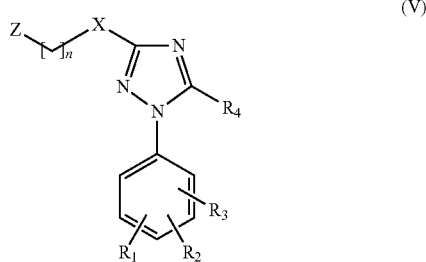

wherein:
$R_1$, $R_2$ and $R_3$ are independently selected from hydrogen, halogen, hydroxyl, alcoxyl, substituted or unsubstituted $C_1$-$C_6$ alkyl, cyano, $NR^aR^b$, $NHCONR^c$, $NHSO_2R^d$, COOH, $COOR^e$, wherein $R^a$ is hydrogen or $C_1$-$C_6$ alkyl and $R^b$, $R^c$, $R^d$ and $R^e$ are independently a $C_1$-$C_6$ alkyl;
$R_4$ is selected from hydrogen, $C_1$-$C_6$ alkyl, cycloalkyl, heterocyclyl and heteroaryl;
X is O or S.
Z is a halogen;
n selected form 1, 2, 3, 4, 5, 6, 7 and 8,
with the proviso that:
$R_4$ is not cyclopropyl; and
when $R_4$ is hydrogen at least one of $R_1$, $R_2$ and $R_3$ is not hydrogen.

The obtained reaction products may, if desired, be purified by conventional methods, such as crystallisation, chromatography and trituration. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form is the crystalline form, including such form in pharmaceutical composition. In the case of salts and solvates the additional ionic and solvent moieties must also be non-toxic. The compounds of the invention may present different polymorphic forms, it is intended that the invention encompasses all such forms.

The present invention further provides pharmaceutical compositions comprising a compound of this invention, or a pharmaceutically acceptable salt, isomer, prodrug or solvate thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

The following examples are given only as further illustration of the invention, they should not be taken as a definition of the limits of the invention.

EXAMPLES

Example 1

Synthesis of 4-[2-(3,4-dichlorophenyl)-5-methyl-1H-1,2,4-triazole-3-ylthio ethyl]morpholine oxalate (compound 1)

A. Synthesis of 3,4-dichlorophenylthiosemicarbazide

A mixture of 3,4-dichlorohydrazine (18.8 mmol) and thiocyanate of potassium (55.7 mmol) was dissolved in water (1 L) and heated for 17 hours. After cooling the product the solid was filtered and dried in vacuo to give 3,4-dichlorophenylthiosemicarbazide (4.20 g, yield=95%). H$^1$NMR (300 MHz, DMSO, 25° C.) δ: 9.37 (s, 1H); 8.30 (s, 1H); 7.84 (s, 1H); 7.60 (s, 1H); 7.40 (d, J=8.7 Hz, 1H); 6.37 (d, J=2.52 Hz. 1H); 6.60 (dd, J=8.67 Hz, J=2.5 Hz. 1H) ppm. EM (ES$^+$) m/z=236 (100%) [M+H]$^+$.

B. Synthesis of 1-acetyl-3,4-(dichlorophenyl)thiosemicarbazide 3,4-dichlorophenylthiosemicarbazide (2.1 mmol) was dissolved in EtOAc (200 mL) under nitrogen and heating to reflux. After cooling at room temperature acetyl chloride (0.23 mL, 3.2 mmol) was added dropwise. The reaction was left under stirring for 16 h. Then the solvent was evaporated under vacuo and the pale pink solid formed was dried in vacuo to give 1-acetyl-3,4-(dichlorofenyl)thiosemicarbazide (0.369 g, yield=63%). $H^1$NMR (300 MHz, DMSO, 25° C.) δ: 10.42 (s, 1H); 8.39 (s, 1H); 8.02 (s, 1H); 7.81 (d, J=2.1 Hz, 1H); 7.68 (d, J=8.7 Hz, 1H); 7.42 (d, J=8.4 Hz); 2.48 (s, 3H) ppm. EM (ES$^+$) m/z=279 (100%) [M+H]$^+$.

C. Synthesis of 1-(3,4-dichlorophenyl)-5-methyl-1H-1,2,4-triazole-3-thiol 1-acetyl-3,4-(dichlorophenyl)thiosemicarbazide (36 mmol) was dissolved in methanol (2 L). A solution of sodium hydroxide 0.5 M with a 25% of methanol was added dropwise until pH 9. After 45 min of stirring at room temperature a solution of hydrochloride acid 1M was added dropwise until pH 2. The pale orange solid formed in the mixture was filtered and dried in vacuo to give 1-(3,4-dichlorophenyl)-5-methyl-1H-1,2,4-triazole-3-thiol (5.99 g, yield=60%. $H^1$NMR (300 MHz, DMSO, 25° C.) δ: 13.99 (s, 1H); 7.94 (d, J=2.4 Hz, 1H); 7.87 (d, J=8.6 Hz, 1H); 7.63 (dd, J=8.7 Hz, J=2.4 Hz, 1H); 2.49 (s, 3H) ppm. EM (ES$^+$) m/z=260 (100%) [M+H]$^+$.

D. Synthesis of 4-[2-(3,4-dichlorophenyl)-5-methyl-1H-1,2,4-triazole-3-yl-thio ethyl]morpholine oxalate 1-(3,4-dichlorophenyl)-5-methyl-1H-1,2,4-triazole-3-thiol (0.4 mmol) was dissolved in methanol (100 mL) at room temperature. A solution of potassium carbonate in water was added dropwise until pH 9. After 15 min. under stirring a solution of 4-(2-chloroethyl)morpholine hydrochloride (0.4 mmol) in water (20 mL) was added. The reaction was left under stirring at room temperature overnight. The methanol was evaporated and after extraction with $CH_2Cl_2$ the organic layer was dried over magnesium sulphate then evaporated and finally purified by chromatographic column to give a dark orange oil. The purified product was dissolved in ether (20 mL) and mixed with a solution of oxalic acid (0.31 mmol) in EtOAc (5 mL) to give 4-(2-(3,4-dichlorophenyl)-5-methyl-1H-1,2,4-triazole-3-ylthio)ethyl)morpholine oxalate (0.147 g, yield=84%) as a white precipitate which was filtered off and dried in vacuo. $H^1$NMR (300 MHz, DMSO, 25° C.) δ: 7.93 (d, J=2.4 Hz, 1H); 7.82 (d, J=8.7 Hz, 1H); 7.61 (dd, J=2.4 Hz, J=8.6 Hz, 1H); 3.66 (t, J=4.6 Hz, 4H); 3.32 (t, J=6.8 Hz, 2H); 2.983 (t, J=7.0 Hz, 2H); 2.78 (brs, 4H); 2.47 (s, 3H) ppm. EM (ES$^+$) m/z=373 (100%) [M+H]$^+$. $C_{17}H_{20}Cl_2N_4O_5S$ (463.0) calc. C, 44.07%; H, 4.35%; N, 12.09%; S=6.92%. found C, 43.79%; H, 4.60%; N, 11.87%; S=6.75%.

The examples 2-6 have been prepared as described for the example 1 using in part D the corresponding 2-chloroethyl amines

Example 2

1-[2-(3,4-dichlorophenyl)-5-methyl-1H-1,2,4-triazole-3-yl-thio ethyl]piperidine oxalate (compound 2)

$H^1$NMR (300 MHz, DMSO, 25° C.) δ: 7.79 (d, J=2.4 Hz, 1H); 7.67 (d, J=8.6 Hz, 1H); 7.48 (dd, J=2.4 Hz, J=8.6 Hz, 1H); 3.25 (m, 2H); 3.14 (m, 2H); 2.95 (m, 4H); 2.31 (s, 3H); 1.54 (m, 4H); 1.33 (m, 2H). EM (ES$^+$) m/z=371 (100%) [M+H]$^+$. $C_{18}H_{22}Cl_2N_4O_4S$ (461) calc. C, 46.86%; H, 4.81%; N, 12.41%; S, 6.95%. found C, 46.38%; H, 4.73%; N, 11.78%; S, 6.69%.

Example 3

1-[2-(3,4-dichlorophenyl)-5-methyl-1H-1,2,4-triazole-3-yl-thio ethyl]pyrrolidine oxalate (compound 3)

$H^1$NMR (300 MHz, DMSO, 25° C.) δ: 7.98 (d, J=2.4 Hz, 1H); 7.86 (d, J=8.6 Hz, 1H); 7.63 (dd, J=2.4 Hz, J=8.7 Hz, 1H); 3.44 (brs, 4H); 3.29 (brs, 4H); 2.51 (s, 3H); 1.92 (brs, 4H). EM (ES$^+$) m/z=357 (100%) [M+H]$^+$. $C_{17}H_{20}Cl_2N_4O_4S$ (447) calc. C, 45.64%; H, 4.51%; N, 12.52%; S, 7.17%. found C, 45.23%; H, 4.48%; N, 11.97%; S, 6.78%.

Example 4

2-[2-(3,4-dichlorophenyl)-5-methyl-1H-1,2,4-triazole-3-yl-thio]-N,N-diisopropyl ethanamine oxalate (compound 4)

$H^1$NMR (300 MHz, DMSO, 25° C.) δ: 7.98 (d, J=2.4 Hz, 1H); 7.86 (d, J=8.4 Hz, 1H); 7.65 (dd, J=2.4 Hz, 1H); 3.68 (m, 2H); 3.40 (m, 4H); 2.50 (s, 3H); 1.31 (m, 12H); 2.50 (s, 3H) ppm. EM (ES$^+$) m/z=387 (100%) [M+H]$^+$. 2[$C_{19}H_{26}Cl_2N_4O_4S$].3$CO_4H_2$ (1044.85) calc. C, 45.98%; H, 5.21%; N, 10.72%; S, 6.14%. found C, 45.89%; H, 5.05%; N, 10.79%; S, 6.05%.

Example 5

2-(1-(3,4-dichlorophenyl)-5-methyl-1H-1,2,4-triazole-3-yl-thio]-N,N-diethyl ethanamine oxalate (compound 5)

$H^1$NMR (300 MHz, DMSO, 25° C.) δ: 7.98 (d, J=2.4 HZ, 1H); 7.86 (d, J=8.6 Hz, 1H); 7.66 (dd, J=2.4 HZ, J=8.6 Hz, 1H); 3.38 (q, J=6.9 Hz, 4H); 3.13 (q, J=7.0 Hz, 2H); 2.51 (s, 3H); 1.21 (m, 2H); 1.09 (t, J=6.9 Hz 6H) ppm. EM (ES$^+$) m/z=359 (100%) [M+H]$^+$. $C_{17}H_{22}Cl_2N_4O_4S$ (449.35). calc. C, 45.44%; H, 4.93%; N, 12.47%; S, 7.14%. found C, 45.08%; H, 4.85%; N, 12.42%; S, 7.01%.

Example 6

1-[2-(1-(3,4-dichlorophenyl)-5-methyl-1H-1,2,4-triazol-3-yl-thio)ethyl]azepane oxalate (compound 6)

$H^1$NMR (300 MHz, DMSO, 25° C.) δ: 7.96 (d, J=2.3 Hz, 1H); 7.84 (d, J=8.6 Hz, 1H); 7.64 (dd, J=2.4 Hz, J=8.6 Hz, 1H); 3.38 (m, 4H); 3.21 (t, J=4.8 Hz, 4H); 2.49 (s, 3H); 1.76 (brs, 4H); 1.58 (brs, 4H) ppm. EM (ES$^+$) m/z=385 (100%) [M+H]$^+$. $C_{19}H_{24}Cl_2N_4O_4S$ (475.39) calc. C, 48.00%; H, 5.09%; N, 11.79%; S, 6.74%. found C, 47.77%; H, 5.19%; N, 11.61%; S, 6.58%.

Example 7

4-[3-(1-(3,4-Dichlorophenyl)-5-methyl-1H-1,2,4-triazol-3-ylthio)propyl]morpholine oxalate (compound 7)

A. Synthesis of 1-(3,4-dichlorophenyl)-5-methyl-1H-1,2,4-triazole-3-thiol

This product was prepared following the steps A to C of the example 1.

B. Synthesis of 3-(3-bromopropylthio)-1-(3,4-dichlorophenyl)-5-methyl-1H-1,2,4-triazole The 1-(3,4-dichlorophenyl)-5-methyl-1H-1,2,4-triazole-3-thiol (5.7 mmol) was dissolved in methanol (1 L) heating under stirring. A solution of potassium carbonate in water (30 mL) was added dropwise until pH 9. After 15 min under stirring 1,3-dibromopropane (2.94 mL, 28 mmol) was added. The reaction was stirred at room temperature for 40 min. Then the solvent was evaporated and the product was purified by chromatographic column using EtOAc to give 3-(3-bromopropylthio)-1-(3,4-dichlorophenyl)-5-methyl-1H-1,2,4-triazole (1.58 g, yield=72%). $H^1$NMR (300 MHz, CDCl$_3$, 25° C.) δ: 7.59 (d, J=2.4 Hz, 1H); 7.56 (d, J=8.6 Hz, 1H); 7.30 (dd, J=2.4 HZ, J=8.6 Hz, 1H); 3.54 (t, J=6.5 Hz, 2H); 3.25 (t, J=6.7 Hz, 2H); 2.5 (s, 3H); 2.32 (m, 2H) ppm.

C. Synthesis of 4-[3-(1-(3,4-dichlorophenyl)-5-methyl-1H-1,2,4-triazol-3-yl-thio)propyl]morpholine oxalate Morpholine (1.3 mmol, 0.011 ml) was dissolved in methanol (20 mL) at room temperature. A solution of carbonate of potassium in water (20 mL) was added dropwise until pH 9. The mixture was stirred for 15 min. Then a solution of 3-(3-bromopropylthio)-1-(3,4-dichlorophenyl)-5-methyl-1H-1,2,4-triazole (1.31 mmol) in methanol (300 mL) was added and the mixture was heated to reflux overnight. The methanol was evaporated and the aqueous solution was extracted with CH$_2$Cl$_2$. The organic layer was dried over MgSO$_4$ then evaporated and finally purified by silica gel chromatography using 10% MeOH/EtOAc to give 3-[1-(3,4-dichlorophenyl)-5-methyl-1H-1,2,4-triazol-3-ylthio)propyl]morpholine as a yellow oil. The purified product was dissolved in ether (30 mL) and mixed with a solution of oxalic acid (0.05 g) in EtOAc (5 mL) to give 4-3-[1-(3,4-dichlorophenyl)-5-methyl-1H-1,2,4-triazol-3-ylthio)propyl]morpholine oxalate (0.23 g, yield 37%) as a white precipitate which was filtered and dried in vacuo system. $H^1$NMR (300 MHz, DMSO, 25° C.) δ: 7.93 (d, J=2.2 Hz, 1H); 7.82 (d, J=8.6 Hz, 1H); 7.613 (dd, J=2.2 Hz, J=8.6 Hz, 1H); 3.71 (brs, 4H); 3.133 (t, J=6.9 Hz, 2H); 2.92 (brs, 6H); 2.48 (s, 3H); 2.02 (m, 2H) ppm. EM (ES$^+$) m/z=387 (100%) [M+H]$^+$. C$_{18}$H$_{22}$Cl$_2$N$_4$O$_5$S (477.36) calc. C, 45.29%; H, 4.65%; N, 11.74%; S, 6.72%. found C, 45.31%; H, 4.61%; N, 11.93%; S, 6.59%.

The examples 8-14 have been prepared as described for example 7 using in part B the corresponding dibromoalkanes and in part C the corresponding amines

Example 8

1-[3-(1-(3,4-dichlorophenyl)-5-methyl-1H-1,2,4-triazol-3-yl-thio)propyl]-4-pyrrolidine oxalate (compound 8)

$H^1$NMR (300 MHz, DMSO, 25° C.) δ: 7.93 (d, J=2.3 Hz, 1H); 7.82 (d, J=8.6 Hz, 1H); 7.62 (dd, J=2.4 Hz, J=8.6 Hz, 1H); 3.17 (m, 8H); 2.48 (s, 3H); 2.07 (m, 2H); 1.89 (brs, 4H) ppm. EM (ES$^+$) m/z=372 (100%) [M+H]$^+$. C$_{18}$H$_{22}$Cl$_2$N$_4$O$_4$S (461.36) calc. C, 46.86%; H, 4.81%; N, 12.14%; S, 6.95%. found C, 46.96%; H, 4.70%; N, 12.31%; S, 6.85%.

Example 9

1-[3-(1-(3,4-dichlorophenyl)-5-methyl-1H-1,2,4-triazol-3-ylthio)propyl]-4-phenylpiperidine oxalate (compound 9)

$H^1$NMR (300 MHz, DMSO, 25° C.) δ: 7.94 (d, J=2.3 Hz, 1H); 7.83 (d, J=8.6 Hz, 1H); 7.62 (dd, J=2.3 Hz, J=8.6 HZ, 1H); 3.19 (m, 4H); 2.19 (m, 2H); 2.72 (m, 1H); 2.11 (m, 2H); 1.83 (m, 4H) ppm. EM (ES$^+$) m/z=461 (100%) [M+H]$^+$. C$_{25}$H$_{28}$Cl$_2$N$_4$O$_4$S (551.49) calc. C, 54.40%; H, 5.12%; N, 10.16%; S, 5.81%. found C, 54.31%; H, 5.03%; N, 10.24%; S, 5.72%.

Example 10

1-[4-(1-(3,4-dichlorophenyl)-5-methyl-1H-1,2,4-triazol-3-yl-thio)butyl]-4-phenylpiperidine oxalate (compound 10)

$H^1$NMR (300 MHz, DMSO, 25° C.) δ: 7.62 (d, J=2.4 Hz, 1H); 7.57 (d, J=8.6 Hz, 1H); 7.28 (m, 4H); 3.18 (t, J=6.9 Hz, 2H); 3.07 (brs, 1H); 3.03 (brs, 1H); 2.52 (s, 3H); 2.48 (m, 1H); 2.41 (t, J=7.3 Hz, 2H); 2.03 (brs, 1H); 2.02 (brs, 1H); 1.79 (m, 8H) ppm. EM (ES$^+$) m/z=475 (100%) [M+H]$^+$. C$_{26}$H$_{30}$Cl$_2$N$_4$O$_4$S (565.51) calc. C, 55.22%; H, 5.35%; N, 9.91%; S, 5.67%. found C, 55.03%; H, 5.50%; N, 9.85%; S, 5.63%.

Example 11

4-[4-(1-(3,4-dichlorophenyl)-5-methyl-1H-1,2,4-triazol-3-yl-thio)butyl]morpholine oxalate (compound 11)

$H^1$NMR (300 MHz, DMSO, 25° C.) δ: 7.92 (d, J=2.4 Hz, 1H); 7.82 (d, J=8.6 HZ, 1H); 7.41 (dd, J=2.4 Hz, J=8.6 Hz, 1H); 3.72 (brs, 4H); 3.11 (brs, 2H); 2.95 (brs, 4H); 2.87 (brs, 2H) 2.48 (s, 3H); 1.71 (brs, 4H) ppm. EM (ES$^+$) m/z=401 (100%) [M+H]$^+$. C$_{19}$H$_{24}$Cl$_2$N$_4$O$_5$S (491.39) calc. C, 46.44%; H, 4.92%; N, 11.40%; S, 6.53%. found C, 49.25%; H, 5.36%; N, 10.78%; S, 5.45%.

Example 12

1-[5-(1-(3,4-dichlorophenyl)-5-methyl-1H-1,2,4-triazol-3-ylthio)pentyl]piperidine oxalate (compound 12)

$H^1$NMR (300 MHz, DMSO, 25° C.) δ: 7.95 (d, J=2.4 Hz, 1H); 7.83 (d, J=8.4 Hz, 1H); 7.60 (dd, J=2.4 Hz, J=8.6 Hz, 1H); 3.09 (m, 6H), 2.93 (m, 2H); 2.46 (s, 3H); 1.68 (brs, 8H); 1.43 (brs, 2H); 1.39 (brs, 2H) EM (ES$^+$) m/z=413 (100%) [M+H]$^+$ C$_{21}$H$_{28}$Cl$_2$N$_4$O$_4$S (503.44) calc. C, 50.10%; H, 5.61%; N, 11.13%; S, 6.37%. found C, 49.89%; H, 5.56%; N, 10.97%; S, 6.09%.

Example 13

4-[5-(1-(3,4-Dichlorophenyl)-5-methyl-1H-1,2,4-triazol-3-ylthio)pentyl]morpholine oxalate (compound 13)

$H^1$NMR (300 MHz, DMSO, 25° C.) δ: 7.92 (d, J=2.1 Hz, 1H); 7.84 (d, 8.6 Hz, 1H); 7.60 (dd, J=2.1 Hz, J=8.6 Hz, 1H); 3.70 (t, J=4.6 Hz, 4H); 3.13 (t, J=7.2 Hz, 2H); 2.51 (s, 3H); 2.42 (t, J=4.2 Hz, 4H); 2.33 (t, J=7.5 Hz, 2H); 1.77 (p, J=7.5 Hz, 2H); 1.49 (m, 4H). EM (ES$^+$) m/z=416 (100%) [M+H]$^+$ C$_{20}$H$_{26}$Cl$_2$N$_4$O$_5$S (505.42) calc. C, 47.53%; H, 5.19%; N, 11.09%; S, 6.34%. found C, 47.27%; H, 5.09%; N, 10.98%; S, 6.07%.

Example 14

1-[5-(1-(3,4-dichlorophenyl)-5-methyl-1H-1,2,4-triazol-3-ylthio)pentyl]pyrrolidine oxalate (compound 14)

$H^1$NMR (300 MHz, DMSO, 25° C.) δ: 7.92 (d, J=2.4 Hz, 1H); 7.83 (d, J=, 8.7 Hz, 1H); 7.60 (dd, J=2.4 Hz, J=8.7 Hz,

1H); 3.12 (m, 4H); 1.89 (m, 2H); 1.69 (m, 4H); 1.41 (m, 2H) ppm. EM (ES$^+$) m/z=399 (100%) [M+H]$^+$. $C_{20}H_{26}Cl_2N_4O_4S$ (489.42) calc. C, 49.08%; H, 5.35%; N, 11.45%; S, 6.55%. found C, 48.97%; H, 5.20%; N, 11.25%; S, 6.80%.

Example 15

1-[2-(1-(3,4-dichlorophenyl)-5-methyl-1H-1,2,4-triazol-3-yl-sulfinyl)ethyl]pyrrolidine (compound 15)

A mixture of 4-(2-(3,4-dichlorophenyl)-5-methyl-1H-1,2,4-triazole-3-ylthio)ethyl)pyrrolidine oxalate (0.7 mmol) and Oxone® (0.67 mmol) was dissolved in water (250 mL) at room temperature under stirring for 3 h. Then a solution of potassium hydroxide 1M was added dropwise until pH 7. After extraction with $CH_2Cl_2$ the organic layer was dried over $MgSO_4$ then evaporated and finally purified by chromatographic on silica gel with 0-10% MeOH/EtOAc to give 4-(2-(1-(3,4-dichlorophenyl)-5-methyl-1H-1,2,4-triazol-3-yl-sulfinyl)ethyl)pyrrolidine (0.082 g, yield 33%) as a colourless oil. H$^1$NMR (300 MHz, CDCl$_3$, 25° C.) δ: 7.64 (d, J=2.5 Hz, 1H); 7.62 (d, J=8.7 Hz, 1H); 7.35 (dd, J=2.4 Hz, J=8.7 Hz, 1H); 3.46 (m, 1H); 3.32 (m, 1H); 3.31 (m, 1H); 2.86 (m 1H) 2.60 (brs, 7H) 1.78 (brs, 4H) ppm. EM (ES$^+$) m/z=373 (100%) [M+H]$^+$ $C_{15}H_{18}Cl_2N_4OS$ (372) calc. C, 48.26%; H, 4.86%; N, 15.01%; S, 8.59%. found C, 48.30%; H, 4.70%; N, 14.81%; S, 8.45%.

The examples 16-18 have been prepared following the procedure described for example 15 using the corresponding 3-thio-1H-1,2,4-triazoles.

Example 16

4-[2-(1-(3,4-dichlorophenyl)-5-methyl-1H-1,2,4-triazol-3-yl-sulfinyl)-ethyl]-morpholine (compound 16)

H$^1$NMR (300 MHz, CDCl$_3$, 25° C.) δ: 7.64 (d, 2.2 Hz, 1H); 7.62 (d, J=8.3 Hz, 1H); 7.35 (dd, J=2.3 Hz, J=8.4 Hz, 1H); 3.68 (t, J=4.5 Hz, 4H); 3.40 (m, 1H); 3.34 (m, 1H); 3.02 (m, 1H); 2.77 (m, 1H); 2.60 (s, 3H); 2.57 (m, 4H) ppm. (ES$^+$) m/z=389 (100%) [M+H]$^+$. $C_{15}H_{18}Cl_2N_4O_2S$ (389.30) calc. C, 46.28%; H, 4.66%; N, 14.39%; S, 8.24%. found C, 46.03%; H, 4.77%; N, 14.13%; S, 7.65%.

Example 17

2-[2-(1-(3,4-dichlorophenyl)-5-methyl-1H-1,2,4-triazol-3-ylsulfinyl]-N,N-diisopropyl ethanamine (compound 17)

H$^1$NMR (300 MHz, CDCl$_3$, 25° C.) δ: 7.64 (d, J=2.4 Hz, 1H); 7.62 (d, J=8.7 Hz, 1H); 7.34 (dd, J=2.4 Hz, J=8.7 Hz, 1H); 3.33 (m, 1H); 3.27 (m, 1H); 3.07 (m, 3H); 2.92 (m, 1H); 2.59 (s, 3H); 1.04 (d, J=6.6 Hz, 6H); 1.00 (d, J=6.5 Hz, 6H) ppm. (ES$^+$) m/z=403 (100%) [M+H]$^+$. $C_{17}H_{24}Cl_2N_4OS$ (403.37) calc. C, 50.62%; H, 6.00%; N, 13.84%; S, 7.95%. found C, 50.66%; H, 5.77%; N, 19.83%; S, 7.45%.

Example 18

1-[4-(1-(3,4-Dichlorophenyl)-5-methyl-1H-1,2,4-triazol-3-ylsulfinyl)butyl]-4-phenylpiperidine (compound 18)

H$^1$NMR (300 MHz, CDCl$_3$, 25° C.) δ: 7.60 (d, J=2.4 Hz, 1H); 7.57 (d, J=8.7 Hz, 1H); 7.30 (m, 6H); 3.40 (m, 2H); 3.31 (m, 2H); 3.10 (m, 4H) 2.61 (m, 4H); 2.49 (s, 3H); 2.09 (m, 2H); 1.71 (m, 5H) ppm. (ES$^+$) m/z=491 (100%) [M+H]$^+$. 2[$C_{24}H_{28}Cl_2N_4OS$].3H$_2$O (1037.00) calc. C, 53.93%; H, 5.85%; N, 10.48%; S, 6.00%. found C, 53.82%; H, 5.96%; N, 10.24%; S, 5.60%.

Example 19

1-[2-(3,4-Dichlorophenyl)-5-methyl-1H-1,2,4-triazol-3-ylsulfonyl)ethyl]pyrrolidine (compound 19)

The example 19 was prepared following the procedure described for example 15 reacting the 4-(2-(3,4-dichlorophenyl)-5-methyl-1H-1,2,4-triazole-3-ylthio)ethyl)pyrrolidine oxalate (0.67 mmol) with Oxone® (1.34 mmol). H$^1$NMR (300 MHz, CDCl$_3$, 25° C.) δ: 7.65 (d, J=2.3 Hz, 1H); 7.63 (d, J=8.6 Hz, 1H); 7.35 (dd, J=2.3 Hz, J=8.7 Hz, 1H); 3.60 (t, J=7.2 Hz, 2H); 3.03 (t, J=7.6, 2H); 2.61 (s, 3H); 2.50 (brs, 4H); 1.70 (brs, 4H) ppm. (ES$^+$) m/z=389 (100%) [M+H]$^+$. $C_{15}H_{18}Cl_2N_4O_2S$ (389.30) calc. C, 46.28%; H, 4.66%; N, 14.34%; S, 8.24%. found C, 46.40%; H, 4.74%; N, 14.28%; S, 7.41%.

The example 20 and 21 were prepared following the procedure described in example 19.

Example 20

2-[1-(3,4-Dichlorophenyl)-5-methyl-1H-1,2,4-triazol-3-ylsulfonyl]-N,N-diethylethanamine (compound 20)

H$^1$NMR (300 MHz, CDCl$_3$, 25° C.) δ: 7.63 (d, J=2.4 Hz, 1H); 7.63 (J=8.5 Hz, 1H); 7.34 (dd, J=2.4 Hz, J=8.7 Hz, 1H); 3.51 (m, 2H); 3.07 (m, 2H); 2.61 (s, 3H); 2.49 (q, J=7.1 Hz, 4H); 0.97 (t, J=7.1 Hz, 6H) ppm. (ES$^+$) m/z=391 (100%) [M+H]$^+$. $C_{15}H_{20}Cl_2N_4O_2S$ (391.32) calc. C, 46.04%; H, 5.15%; N, 14.32%; S, 8.19%. found C, 46.09%; H, 5.25%; N, 14.24%; S, 8.20%.

Example 21

4-[4-(1-(3,4-Dichlorophenyl)-5-methyl-1H-1,2,4-triazol-3-yl-sulfonyl)-butyl]morpholine (compound 21)

H$^1$NMR (300 MHz, CDCl$_3$, 25° C.) δ: 7.65 (d, J=2.4 Hz, 1H); 7.61 (d, J=8.6 Hz, 1H); 7.34 (dd, J=2.4 Hz, J=8.6 Hz, 1H); 4.40 (m, 2H); 3.72 (m, 2H); 3.32 (m, 6H); 3.09 (m, 2H); 2.8 (m, 4H); 2.58 (s, 3H); 2.16 (m, 2H); 1.92 (m, 2H) ppm. (ES$^+$) m/z=433 (100%) [M+H]$^+$. $C_{17}H_{22}Cl_2N_4O_3S.2H_2O$ (469.38) calc. C, 42.68%; H, 5.69%; N, 11.71%; S, 6.70%. found C, 42.94%; H, 5.44%; N, 11.70%; S, 6.18%.

Example 22

1-[2-(3,4-Dichlorophenyl)-5-methyl-1H-1,2,4-triazol-3-yloxy)ethyl]piperidine (compound 22)

A. Synthesis of 1-(3,4-Dichlorophenyl)-5-methyl-1H-1,2,4-triazole-3-ol

This product was prepared following the steps from A to C of example 1 using potassium cyanate in step A and using ethanol as solvent under N$_2$ at 60° C. in step C.

B. 1-[2-(3,4-Dichlorophenyl)-5-methyl-1H-1,2,4-triazol-3-yloxy)ethyl]piperidine 1-(3,4-Dichlorophenyl)-5-methyl-1H-1,2,4-triazole-3-ol (0.41 mmol) was dissolved in methanol (150 mL) at room temperature. A solution of potassium carbonate in water (30 mL) was added dropwise until pH 9. After 15 min under stirring a solution of 4-(2-chloroethyl)piperidine hydrochloride (0.62 mmol) in water (100 mL) was added. The reaction was stirred at room temperature overnight. The methanol was evaporated and after extraction with $CH_2Cl_2$ the organic layer was dried over $MgSO_4$ then evaporated and finally purified by chromatography in silica gel to give 1-[2-(3,4-dichlorophenyl)-5-methyl-1H-1,2,4-triazol-3-yloxy)methyl]piperidine (0.03 g, yield 20%) as a dark orange oil. $H^1$NMR (300 MHz, $CDCl_3$, 25° C.) δ: 7.53 (d, J=2.4 Hz, 1H); 7.48 (d, J=8.6 Hz, 1H); 7.23 (d, J=2.4 Hz, 1H); 4.33 (t, J=5.9 Hz, 2H); 2.71 (t, J=5.9 Hz, 2H); 2.44 (t, J=4.9 Hz, 4H); 2.40 (s, 3H); 1.51 (q, J=5.5 Hz, 4H); 1.34 (m, 2H) ppm. EM ($ES^+$) m/z=355 (100%) $[M+H]^+$. $C_{16}H_{20}Cl_2N_4O$ (355.26) calc. C, 54.09%; H, 5.67%; N, 15.77%. found C, 53.80%; H, 5.72%; N, 15.48%.

The examples 23-30 have been prepared as described for example 22 using in part B the corresponding 2-chloroethyl amines. The example 30 has been prepared following the procedure described for the preparation of example 7 starting with 5-methyl-1-phenyl-1H-1,2,4-triazol-3-ol with the corresponding dibromoalkane (part B) and amine (part C).

Example 23

2-[1-(3,4-Dichlorophenyl)-5-methyl-1H-1,2,4-triazol-3-yloxy]-N,N-diethylethanamine (compound 23)

$H^1$NMR (300 MHz, $CDCl_3$, 25° C.) δ: 7.53 (d, J=2.3 Hz, 1H); 7.47 (d, J=8.6 Hz, 1H); 7.23 (dd, J=2.3 Hz, J=8.6 Hz, 1H); 4.28 (t, J=6.6 Hz, 2H); 2.83 (t, J=6.3 Hz, 2H); 2.56 (q, J=7.1 Hz, 4H); 2.40 (s, 3H); 0.99 (t, 7.1 Hz, 6H) ppm. EM ($ES^+$) m/z=343 (100%) $[M+H]^+$. $3[C_{15}H_{20}Cl_2N_4O].2H_2O$ (1065.79) calc. C, 50.71%; H, 6.05%; N, 15.81%. found C, 50.70%; H, 5.82%; N, 16.12%.

Example 24

1-[2-(1-(3,4-Dichlorophenyl)-5-methyl-1H-1,2,4-triazol-3-yloxy)ethyl]pyrrolidine (compound 24)

$H^1$NMR (300 MHz, $CDCl_3$, 25° C.) δ: 7.58 (d, J=2.4 Hz, 1H); 7.53 (d, J=8.7 Hz, 1H); 7.28 (dd, J=2.4 Hz, J=8.7 Hz, 1H); 4.40 (t, J=5.9 Hz, 2H); 2.90 (t, 5.8 Hz, 2H); 2.63 (m, 4H); 2.45 (s, 3H); 1.78 (p, J=3.2 Hz, 4H) ppm. EM ($ES^+$) m/z=341 (100%) $[M+H]^+$. $C_{15}H_{18}Cl_2N_4O$ (341.24) calc. C, 52.80%; H, 5.32%; N, 16.42%. found C, 51.86%; H, 5.26%; N, 16.13%.

Example 25

4-[2-(1-(3,4-Dichlorophenyl)-5-methyl-1H-1,2,4-triazol-3-yloxy)ethyl]morpholine oxalate (compound 25)

$H^1$NMR (300 MHz, DMSO, 25° C.) δ: 7.91 (d, J=2.4 Hz, 1H); 7.82 (J=8.7 Hz, 1H); 7.60 (dd, J=2.4 Hz, J=8.7 Hz, 1H); 4.45 (t, J=5.1 Hz, 2H); 3.70 (t, J=4.6 Hz, 4H); 3.13 (t, J=5.1 Hz, 2H); 2.89 (m, 4H); 2.49 (s, 3H) ppm. EM ($ES^+$) m/z=357 (100%) $[M+H]^+$. $C_{17}H_{20}Cl_2N_4O_6$ (447.27) calc. C, 45.65%; H, 4.51%; N, 12.53%. found C, 45.48%; H, 4.43%; N, 12.27%.

Example 26

2-(5-methyl-1-phenyl-1H-1,2,4-triazol-3-yloxy)-N,N-diethyl ethanamine (compound 26)

$H^1$NMR (300 MHz, $CDCl_3$, 25° C.) δ: 7.42 (m, 5H); 4.35 (t, J=6.2 Hz, 2H); 2.90 (t, J=6.2 Hz, 2H); 2.63 (q, t=7.1 Hz, 4H); 2.43 (s, 3H); 1.05 (t, J=7.1 Hz, 6H) ppm. EM ($ES^+$) m/z=275 (100%) $[M+H]^+$. $C_{15}H_{22}N_4O$ (274.36) calc. C, 65.67%; H, 8.08%; N, 20.42%. found C, 65.39%; H, 7.92%; N, 20.26%.

Example 27

1-[2-(5-methyl-1-phenyl-1H-1,2,4-triazol-3-yloxy) ethyl]pyrrolidine (compound 27)

$H^1$NMR (300 MHz, $CDCl_3$, 25° C.) δ: 7.43 (m, 5H); 4.41 (t, J=5.9 Hz, 2H); 2.90 (t, J=5.9 Hz, 2H); 2.64 (m, 4H); 2.42 (s, 3H); 1.78 (m, 4H) ppm. EM ($ES^+$) m/z=273 (100%) $[M+H]^+$. $C_{15}H_{20}N_4O$ (272.35) calc. C, 66.15%; H, 7.40%; N, 20.57%. found C, 65.87%; H, 7.22%; N, 20.39%.

Example 28

4-[2-(5-methyl-1-phenyl-1H-1,2,4-triazol-3-yloxy) ethyl]morpholine (compound 28)

$H^1$NMR (300 MHz, $CDCl_3$, 25° C.) δ: 7.43 (m, 5H); 4.42 (t, 5.6 Hz, 1H); 3.71 (t, J=4.6 Hz, 4H); 2.81 (t, J=5.5 Hz, 2H); 2.58 (m, 4H); 2.44 (s, 3H) ppm. EM ($ES^+$) m/z=289 (100%) $[M+H]^+$.

Example 29

1-[2-(5-methyl-1-phenyl-1H-1,2,4-triazol-3-yloxy) ethyl]piperidine (compound 29)

$H^1$NMR (300 MHz, $CDCl_3$, 25° C.) δ: 7.43 (m, 5H); 4.41 (t, J=5.9 Hz, 2H); 2.79 (t, J=5.9 Hz, 2H); 2.51 (m, 4H); 2.43 (s, 3H); 1.57 (m, 4H); 1.42 (m, 2H) ppm. EM ($ES^+$) m/z=287 (100%) $[M+H]^+$. $C_{16}H_{22}N_4O$ (286.37) calc. C, 67.11%; H, 7.74%; N, 19.56%. found C, 66.96%; H, 7.65%; N, 19.37%.

Example 30

4-[4-(5-methyl-1-phenyl-1H-1,2,4-triazol-3-yloxy) butyl]morpholine (compound 30)

$H^1$NMR (300 MHz, $CDCl_3$, 25° C.) δ: 7.43 (m, 5H); 4.28 (t, J=6.1 Hz, 2H); 3.70 (t, J=4.6 Hz, 4H); 2.43 (s, 3H); 2.39 (m, 6H); 1.83 (m, 2H); 1.65 (m, 2H) ppm. EM ($ES^+$) m/z=317 (100%) $[M+H]^+$. $C_{17}H_{24}N_4O_2$ (316.40) calc. C, 64.53%; H, 7.65%; N, 17.71%. found C, 63.56%; H, 7.45%; N, 17.40%.

Example 31

4-[2-(3,4-Dichlorophenyl)-5-methyl-1H-1,2,4-triazole-3-ylthio)ethyl]morpholine hydrochloride (compound 31)

The example 31 was prepared as described for example 1. In part D of the procedure, the chromatographied product was dissolved in ether and the solution was saturated with chloride acid gas. The resulting suspension was filtered off and dried in vacuo. $H^1$NMR (300 MHz, DMSO, 25° C.) δ: 11.98 (brs, 1H); 9.99 (brs, 3H); 8.00 (d, J=2.4 Hz, 1H); 7.84 (d, J=8.6 Hz, 1H); 7.68 (dd, J=2.4 Hz, J=8.6 Hz, 1H); 3.89 (m, 4H); 3.49 (m, 6H); 3.12 (m, 2H); 2.50 (s, 3H) ppm. $C_{15}H_{19}N_4Cl_3OS.HCl.1.5H_2O$ (473.25) calc. C, 38.07%; H, 4.90%; N, 11.84%; S, 6.78%. Found C, 37.93%; H, 4.94%; N, 11.64%; S, 6.00%.

The examples 32-39 have been prepared as described for example 1 using the corresponding hydrazine in part A.

Example 32

1-[2-(1-(3,4-dichlorophenyl)-5-methyl-1H-1,2,4-triazol-3-ylthio)ethyl]-4-methylpiperidinium oxalate (compound 32)

H$^1$NMR (300 MHz, DMSO, 25° C.) δ: 7.97 (d, J=2.3 Hz, 1H); 7.84 (d, J=8.6 Hz, 1H); 7.65 (dd, J=2.4 Hz, J=8.6, 1H); 3.45 (m, 4H); 3.36 (m, 2H); 2.92 (m, 2H); 2.48 (s, 3H); 1.75 (m, 2H); 1.59 (m, 1H); 1.37 (m, 2H); 0.90 (d, J=3.8 Hz, 3H) ppm. EM (ES$^+$) m/z=385 (100%) [M+H]$^+$. 5[C$_{19}$H$_{24}$Cl$_2$N$_4$O$_5$S].3C$_2$H$_2$O$_4$ (2647.05). caldc. C, 45.83%; H, 4.80%; N, 10.58%; S, 6.06%. found C, 45.61%; H, 4.74%; N, 10.61%; S, 6.08%.

Example 33

4-[2-(5-methyl-1-phenyl-1H-1,2,4-triazol-3-ylthio)ethyl]morpholinium oxalate (compound 33)

H$^1$NMR (300 MHz, DMSO, 25° C.) δ: 7.51 (m, 5H); 3.68 (t, J=4.5 Hz, 4H); 3.36 (t, J=6.1 Hz, 2H); 3.04 (t, J=6.3 Hz, 2H); 2.84 (brs, 4H); 2.49 (s, 3H) ppm. 2[C$_{17}$H$_{22}$N$_4$O$_5$S].C$_2$H$_2$O$_4$ (878.93). caldc. C, 49.19%; H, 5.28%; N, 12.75%; S, 7.30%. found C, 48.86%; H, 5.49%; N, 12.47%; S, 7.45%.

Example 34

4-[2-(1-(4-chlorophenyl)-5-methyl-1H-1,2,4-triazol-3-ylthio)ethyl]morpholinium oxalate (compound 34)

H$^1$NMR (300 MHz, DMSO, 25° C.) δ: 7.62 (brs, 4H); 3.68 (t, J=4.4 Hz, 4H); 3.33 (t, J=6.9 Hz, 2H); 3.04 (t, J=7.8 Hz, 2H); 2.84 (brs, 4H); 2.44 (s, 3H) ppm. EM (ES$^+$) m/z=339 (100%) [M+H]$^+$. C$_{17}$H$_{21}$ClN$_4$O$_5$S (428.89). caldc. C, 47.61%; H, 4.94%; N, 13.06%; S, 7.48%. found C, 47.50%; H, 4.91%; N, 13.12%; S, 7.26%.

Example 35

N-[2-(1-(3-chlorophenyl)-5-methyl-1H-1,2,4-triazol-3-ylthio)ethyl]-N,N-diisopropylpropan-2-aminium oxalate (compound 35)

H$^1$NMR (300 MHz, CDCl$_3$, 25° C.) δ: 7.43 (m, 3H); 7.31 (m, 1H); 3.73 (m, 2H); 3.54 (m, 2H); 3.46 (m, 2H); 2.50 (s, 3H); 1.43 (d, J=6.0 Hz, 12H) ppm. EM (ES$^+$) m/z=353 (100%) [M+H]$^+$.

Example 36

1-[2-(1-(3-chlorophenyl)-5-methyl-1H-1,2,4-triazol-3-ylthio)ethyl]piperidinium oxalate (compound 36)

H$^1$NMR (300 MHz, DMSO, 25° C.) δ: 7.73 (s, 1H); 7.58 (brs, 3H); 3.44 (m, 2H); 3.34 (m, 2H); 3.15 (brs, 4H); 2.49 (s, 3H); 1.70 (m, 4H); 1.50 (brs, 2H) ppm. EM (ES$^+$) m/z=337 (100%) [M+H]$^+$. C$_{18}$H$_{23}$ClN$_4$O$_4$S.3H$_2$O (504.39). caldc. C, 50.64%; H, 5.43%; N, 13.12%; S, 7.51%; Cl, 8.30%. found C, 50.37%; H, 5.42%; N, 12.99%; S, 7.37%; Cl, 8.88%.

Example 37

4-[2-(1-(3-chlorophenyl)-5-methyl-1H-1,2,4-triazol-3-ylthio)ethyl]morpholinium oxalate (compound 37)

H$^1$NMR (300 MHz, DMSO, 25° C.) δ: 7.71 (s, 1H); 7.57 (brs, 3H); 3.66 (m, 4H); 3.34 (m, 2H); 2.96 (m, 2H); 2.77 (brs, 4H); 2.46 (s, 3H) ppm. EM (ES$^+$) m/z=339 (100%) [M+H]$^+$. C$_{17}$H$_{21}$ClN$_4$O$_5$S (428.89). caldc. C, 47.61%; H, 4.94%; N, 13.06%; S, 7.48%; Cl, 8.27%. found C, 47.54%; H, 4.90%; N, 12.87%; S, 7.35%; Cl, 8.52%.

Example 38

4-[2-(1-(3-chlorophenyl)-5-methyl-1H-1,2,4-triazol-3-ylthio)ethyl]pyrrolidinium oxalate (compound 38)

H$^1$NMR (300 MHz, DMSO, 25° C.) δ: 7.74 (s, 1H); 7.60 (brs, 3H); 3.41 (brs, 6H); 3.25 (brs, 2H); 2.49 (s, 3H); 1.84 (brs, 4H) ppm. EM (ES$^+$) m/z=323 (100%) [M+H]$^+$. C$_{17}$H$_{21}$ClN$_4$O$_4$S (412.89). caldc. C, 49.45%; H, 5.13%; N, 13.57%; S, 7.77%. found C, 49.21%; H, 5.08%; N, 13.28%; S, 7.55%.

Example 39

2-[1-(3-chlorophenyl)-5-methyl-1H-1,2,4-triazol-3-ylthio]-N,N-diethylethanaminium oxalate (compound 39)

H$^1$NMR (300 MHz, DMSO, 25° C.) δ: 7.74 (s, 1H); 7.59 (s, 3H); 3.37 (m, 4H); 3.11 (m, 4H); 2.49 (brs, 3H); 1.19 (m, 6H) ppm. EM (ES$^+$) m/z=325 (100%) [M+H]$^+$. C$_{17}$H$_{23}$ClN$_4$O$_4$S (414.91). caldc. C, 49.21%; H, 5.59%; N, 13.50%; S, 7.73%; Cl, 8.54%. found C, 48.97%; H, 5.40%; N, 13.39%; S, 7.65%; Cl, 8.59%.

The example 40-42 have been prepared as describe for example 7 using the corresponding 1,4-dibromoalkane in part B.

Example 40

4-[1-(3,4-dichlorophenyl)-5-methyl-1H-1,2,4-triazol-3-ylthio]-N,N-diethylbutan-1-amine (compound 40)

H$^1$NMR (300 MHz, CDCl$_3$, 25° C.) δ: 7.60 (d, J=2.4 Hz, 1H); 7.53 (d, J=8.6 Hz, 1H); 7.31 (dd, J=2.4 Hz, J=8.6 Hz, 1H); 3.15 (t, J=7.0 Hz, 2H); 2.59 (q, J=7.1 Hz, 4H); 2.51 (m, 5H); 1.69 (m, 4H); 1.06 (t, J=7.1 Hz, 6H) ppm. EM (ES$^+$) m/z=386 (100%) [M+H]$^+$. C$_{17}$H$_{24}$Cl$_2$N$_4$S.H$_2$O (405.39). caldc. C, 50.37%; H, 6.46%; N, 13.82%; S, 7.91%. found C, 49.88%; H, 6.81%; N, 13.55%; S, 8.64%.

Example 41

1-[4-(1-(3,4-dichlorophenyl)-5-methyl-1H-1,2,4-triazol-3-ylthio)butyl]piperidine (compound 41)

H$^1$NMR (300 MHz, CDCl$_3$, 25° C.) δ: 7.59 (d, J=2.4 Hz, 1H); 7.56 (d, J=8.6 Hz, 1H); 7.31 (dd, J=2.4 Hz, J=8.6 Hz, 1H); 3.14 (t, J=6.5 Hz, 2H); 2.62 (brs, 4H); 2.55 (m, 2H); 2.50 (s, 3H); 1.77 (m, 4H); 1.49 (brs, 2H) ppm. EM (ES$^+$) m/z=399 (100%) [M+H]$^+$. C$_{18}$H$_{24}$Cl$_2$N$_4$S.H$_2$O (417.40). caldc. C, 49.65%; H, 6.45%; N, 12.87%; S, 7.36%. found C, 49.27%; H, 6.58%; N, 12.70%; S, 7.51%.

Example 42

1-[4-(1-(3,4-dichlorophenyl)-5-methyl-1H-1,2,4-triazol-3-ylthio)butyl]pyrrolidine (compound 42)

H$^1$NMR (300 MHz, CDCl$_3$, 25° C.) δ: 7.59 (d, J=2.4 Hz, 1H); 7.56 (d, J=8.6 Hz, 1H); 7.33 (dd, J=2.4 Hz, J=8.6 Hz, 1H); 3.13 (t, J=6.9 Hz, 2H); 2.96 (brs, 4H); 2.83 (m, 2H); 2.50 (s, 3H); 1.98 (m, 4H) ppm. EM (ES$^+$) m/z=385 (100%) [M+H]$^+$. C$_{17}$H$_{22}$Cl$_2$N$_4$S.3H$_2$O (439.40). caldc. C, 46.47%; H, 6.42%; N, 12.75%; S, 7.30%. found C, 46.45%; H, 5.99%; N, 12.55%; S, 6.84%.

The examples 43-46 have been prepared as described for example 15.

Example 43

2-[1-(3,4-dichlorophenyl)-5-methyl-1H-1,2,4-triazol-3-ylsulfinyl]-N,N-diethylethanamine (compound 43)

H$^1$NMR (300 MHz, CDCl$_3$, 25° C.) δ: 7.64 (d, J=2.5 HZ, 1H); 7.62 (d, J=8.7 Hz, 1H); 7.35 (dd, J=2.4 Hz, J=8.7 Hz, 1H); 3.52 (m, 2H); 3.08 (m, 1H); 2.85 (m, 1H); 2.58 (m, 7H); 1.02 (t, J=7.1 Hz, 6H) ppm. EM (ES$^+$) m/z=374 (100%) [M+H]$^+$. C$_{15}$H$_{20}$Cl$_2$N$_4$OS (375.32). caldc. C, 48.00%; H, 5.37%; N, 14.93%; S, 8.54%. found C, 47.71%; H, 5.20%; N, 14.62%; S, 8.34%.

Example 44

1-[2-(1-(3-chlorophenyl)-5-methyl-1H-1,2,4-triazol-3-yl-sulfinyl)ethyl]pyrrolidine (compound 44)

H$^1$NMR (300 MHz, CDCl$_3$, 25° C.) δ: 7.50 (brs, 1H); 7.47 (brs, 1H); 7.46 (brs, 1H); 7.36 (m, 1H); 3.48 (m, 1H); 3.32 (m, 1H); 3.13 (m, 1H); 2.80 (m, 1H); 2.56 (brs, 7H); 1.76 (brs, 4H) ppm. EM (ES$^+$) m/z=339 (100%) [M+H]$^+$. C$_{15}$H$_{19}$ClN$_4$OS (338.86). caldc. C, 53.17%; H, 5.65%; N, 16.53%; S, 9.46%; Cl, 10.46%. found C, 53.25%; H, 5.80%; N, 16.76%; S, 9.21%; Cl, 10.26%.

Example 45

1-[2-(1-(3-chlorophenyl)-5-methyl-1H-1,2,4-triazol-3-yl-sulfinyl)ethyl]morpholine (compound 45)

H$^1$NMR (300 MHz, CDCl$_3$, 25° C.) δ: 7.48 (m, 3H); 7.36 (brs, 1H); 3.66 (m, 4H); 3.42 (m, 1H); 3.32 (m, 1H); 3.01 (m, 1H); 2.77 (m, 1H); 2.58 (s, 3H); 2.50 (m, 4H) ppm. EM (ES$^+$) m/z=355 (100%) [M+H]$^+$. C$_{15}$H$_{19}$ClN$_4$O$_2$S (354.85). caldc. C, 50.77%; H, 5.40%; N, 15.79%; S, 9.04%. found C, 50.58%; H, 5.25%; N, 15.62%; S, 9.31%.

Example 46

1-[2-(1-(3-chlorophenyl)-5-methyl-1H-1,2,4-triazol-3-yl-sulfinyl)ethyl]-N,N-diethylamine (compound 46)

H$^1$NMR (300 MHz, CDCl$_3$, 25° C.) δ: 7.50 (brs, 1H); 7.47 (m, 2H); 7.36 (m, 1H); 3.40 (m, 2H); 3.06 (m, 2H); 2.87 (m, 1H); 2.58 (m, 7H); 1.01 (t, J=7.1 Hz, 6H) ppm. EM (ES$^+$) m/z=341 (100%) [M+H]$^+$. C$_{15}$H$_{21}$ClN$_4$OS (340.87). caldc. C, 52.85%; H, 6.21%; N, 16.44%; S, 9.41%. found C, 52.76%; H, 6.50%; N, 16.22%; S, 9.71%.

The examples 47-49 have been prepared as described for example 19.

Example 47

1-[2-(1-(3-chlorophenyl)-5-methyl-1H-1,2,4-triazol-3-yl-sulfonyl)ethyl]pyrrolidine (compound 47)

H$^1$NMR (300 MHz, CDCl$_3$, 25° C.) δ: 7.58 (m, 3H); 7.47 (m, 1H); 3.60 (t, J=7.3 Hz, 2H); 3.03 (t, J=7.2 Hz, 2H); 2.61 (s, 3H); 2.50 (brs, 4H); 1.70 (m, 4H) ppm. EM (ES$^+$) m/z=355 (100%) [M+H]$^+$. C$_{15}$H$_{19}$ClN$_4$O$_2$S (3548.85). caldc. C, 50.77%; H, 5.40%; N, 15.79%; S, 9.04%. found C, 50.48%; H, 5.25%; N, 15.62%; S, 9.31%.

Example 48

1-[2-(1-(3-chlorophenyl)-5-methyl-1H-1,2,4-triazol-3-yl-sulfonyl)ethyl]-N,N-diisopropilamine (compound 48)

H$^1$NMR (300 MHz, CDCl$_3$, 25° C.) δ: 7.51 (m, 3H); 7.38 (m, 1H); 3.47 (m, 2H); 3.01 (m, 4H); 2.61 (brs, 3H); 0.98 (m, 12H) ppm. (ES$^+$) m/z=385 (100%) EM [M+H]$^+$. C$_{17}$H$_{25}$ClN$_4$O$_2$S (384.92). caldc. C, 53.04%; H, 6.55%; N, 14.56%; S, 8.33%. found C, 53.19%; H, 6.26%; N, 14.42%; S, 8.51%.

Example 49

1-[2-(1-(3-chlorophenyl)-5-methyl-1H-1,2,4-triazol-3-yl-sulfonyl)ethyl]-N,N-diethylamine (compound 49)

H$^1$NMR (300 MHz, CDCl$_3$, 25° C.) δ: 7.49 (m, 3H); 7.37 (m, 1H); 3.63 (t, J=4.8 Hz, 2H); 3.07 (m, 2H); 2.60 (s, 3H); 2.50 (m, 4H); 0.97 (t, J=7.0 Hz, 6H) ppm. EM (ES$^+$) m/z=357 (100%) [M+H]$^+$. C$_{15}$H$_{21}$ClN$_4$O$_2$S (356.87). caldc. C, 50.48%; H, 5.93%; N, 15.70%; S, 8.99%. found C, 50.25%; H, 5.84%; N, 15.60%; S, 9.20%.

Biological Activity Examples

Compounds 1-30 synthesized according to the procedures described above, were tested for their activity as sigma-1 inhibitors. The following protocol was followed:

Brain membrane preparation and binding assays for the σ1-receptor were performed as described (DeHaven-Hudkins et al., 1992) with some modifications. In brief, guinea pig brains were homogenized in 10 vols. (w/v) of Tris-HCl 50 mM 0.32 M sucrose, pH 7.4, with a Kinematica Polytron PT 3000 at 15000 r.p.m. for 30 s. The homogenate was centrifuged at 1000 g for 10 min at 4° C. and the supernatants collected and centrifuged again at 48000 g for 15 min at 4° C. The pellet was resuspended in 10 volumes of Tris-HCl buffer (50 mM, pH 7.4), incubated at 37° C. for 30 min, and centrifuged at 48000 g for 20 min at 4° C. Following this, the pellet was resuspended in fresh Tris-HCl buffer (50 mM, pH 7.4) and stored on ice until use.

Each assay tube contained 10 μL of [$^3$H](+)-pentazocine (final concentration of 0.5 nM), 900 μL of the tissue suspension to a final assay volume of 1 mL and a final tissue concentration of approximately 30 mg tissue net weight/mL. Non-specific binding was defined by addition of a final concentration of 1 μM haloperidol. All tubes were incubated at 37° C. for 150 min before termination of the reaction by rapid filtration over Schleicher & Schuell GF 3362 glass fibre filters [previously soaked in a solution of 0.5% polyethylenimine for at least 1 h]. Filters were then washed with four times with 4 mL of cold Tris-HCl buffer (50 mM, pH 7.4). Following addition of scintillation cocktail, the samples were allowed to equilibrate overnight. The amount of bound radioactivity was determined by liquid scintillation spectrometry using a Wallac Winspectral 1414 liquid scintillation counter. Protein concentrations were determined by the method of Lowry et al. (1951).

REFERENCES

DeHaven-Hudkins, D. L., L. C. Fleissner, and F. Y. Ford-Rice, 1992, Characterization of the binding of [$^3$H](+)pentazocine to σ recognition sites in guinea pig brain, *Eur. J. Pharmacol.* 227, 371-378.

Lowry, O. H., N. J. Rosebrough, A. L. Farr, and R. J. Randall, 1951, Protein measurement with the Folin phenol reagent, *J. Biol. Chem.*, 193, 265.

The results are summarized in the following table I:

TABLE I

| compound no. | Sigma-1 Inhibition percent (0.1 µM) | Sigma-1 Inhibition percent (0.01 µM) | Sigma-1 Ki (nm) Displ. $10^{-7}$ M ($10^{-8}$ M) |
|---|---|---|---|
| 1 | 107.4 | 102.1 | 1.1 |
| 2 | 109.3 | 105.2 | 0.8 |
| 3 | 106.4 | 102.7 | 1.4 |
| 4 | 108.8 | 105.3 | 1.1 |
| 5 | 109.3 | 104.4 | 1.1 |
| 6 | 99.2 | 90.6 | |
| 7 | 85.5 | 67.8 | 8.2 |
| 8 | 82.5 | 57.4 | 2.1 |
| 9 | 89 | 74.2 | 9 |
| 10 | 88.1 | 27.3 | |
| 11 | 66.9 | 14.5 | |
| 12 | 82.8 | 52.1 | |
| 13 | 58.2 | 4.3 | |
| 14 | 52.5 | 6 | |
| 15 | 88.9 | 47.2 | 7 |
| 16 | 42 | 28.6 | |
| 17 | 93.9 | 62.3 | 4 |
| 18 | 37.2 | −39.5 | |
| 19 | 96.4 | 71.8 | 2.2 |
| 20 | 82.1 | 51.2 | 16.7 |
| 21 | 20.5 | 8.3 | |
| 22 | 94.8 | 54.3 | 3.1 ± 1.6 |
| 23 | 85 | 32.2 | |
| 24 | 91.8 | 39.5 | |
| 25 | 83.8 | 33.8 | |
| 26 | 15.2 | 7.3 | |
| 27 | 30.4 | 8.1 | |
| 28 | −3.4 | −20.9 | |
| 29 | 46.1 | 5.8 | |
| 30 | 18.3 | −15.1 | |

As can be seen from the values given in table 1 the substituted 1,2,4-triazole derivatives of the invention are particularly suitable for inhibiting the sigma-1 receptor.

The invention claimed is:

1. Method of treating or preventing a sigma-1 receptor mediated disease or condition which method comprises administering to a patient in need of such a treatment a therapeutically effective amount of a compound of formula (I)

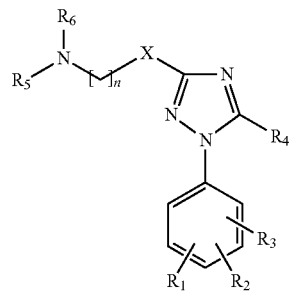

wherein:
$R_1$, $R_2$ and $R_3$ are independently selected from the group consisting of hydrogen, halogen, hydroxyl, alcoxyl, substituted or unsubstituted $C_1$-$C_6$ alkyl, cyano, $NR^a R^b$, $NHCONR^c$, $NHSO_2 R^d$, COOH, $COOR^e$, wherein $R^a$ is hydrogen or $C_1$-$C_6$ alkyl and $R^b$, $R^c$, $R^d$ and $R^e$ are independently a $C_1$-$C_6$ alkyl;
$R_4$ is selected from the group consisting of hydrogen, $C_1$-$C_6$ alkyl, cycloalkyl, heterocyclyl and heteroaryl;
$R_5$ and $R_6$ are independently a $C_1$-$C_6$ alkyl or form, together with the nitrogen atom to which they are attached, a substituted or unsubstituted heterocyclyl group;
X is selected from the group consisting of —S—, —SO—, —$SO_2$— and O; and
n is an integer selected from 1, 2, 3, 4, 5, 6, 7 and 8,
or a pharmaceutically acceptable salt, stereoisomer, or solvate thereof;
wherein said disease or condition is pain.

2. Method of treatment of claim 1, wherein said compound of formula (I) is used as pharmacological tool, as anxiolytic or immunosuppressant.

3. The method according to claim 1 wherein pain is selected from the group consisting of neuropathic pain, inflammatory pain and other pain conditions involving allodynia and/or hyperalgesia.

4. The method according to claim 1 wherein at least one of $R_1$ to $R_3$ is hydrogen in the compound of formula (I).

5. The method according to claim 4 wherein two of $R_1$ to $R_3$ are hydrogen or halogen.

6. The method according to claim 5 wherein the halogen is chloride.

7. The compound according to claim 1 wherein $R_4$ is a $C_1$-$C_6$ alkyl.

8. The method according to claim 7 wherein $R_4$ is methyl.

9. The method according to claim 1 wherein $R_5$ and $R_6$ are independently a $C_1$-$C_6$ alkyl.

10. The method according to claim 9 wherein $R_5$ and $R_6$ are independently ethyl or isopropyl.

11. The method according to claim 1 wherein $R_5$ and $R_6$ form, together with the nitrogen to which they are attached, a substituted or unsubstituted heterocyclyl group.

12. The method according to claim 11 wherein the heterocyclic group is selected from the group consisting of pyrrolidine, piperidine, azepane and morpholine.

13. The compound according to claim 12 wherein n is 1, 2, 3, 4 or 5.

14. The method according to claim 1, wherein the compound of formula (I) is selected from the group consisting of:
  4-{2-[1-(3,4-dichlorophenyl)-5-methyl-1H-1,2,4-triazole-3-ylthio]ethyl}morpholine;

1-{2-[1-(3,4-dichlorophenyl)-5-methyl-1H-1,2,4-triazole-3-yl-thio]ethyl}piperidine;
1-{2-[1-(3,4-dichlorophenyl)-5-methyl-1H-1,2,4-triazole-3-yl-thio]ethyl}pyrrolidine;
2-[1-(3,4-dichlorophenyl)-5-methyl-1H-1,2,4-triazole-3-yl-thio]-N,N-diisopropyl ethanamine;
2-[1-(3,4-dichlorophenyl)-5-methyl-1H-1,2,4-triazole-3-yl-thio]-N,N-diethyl ethanamine;
1-[2-(1-(3,4-dichlorophenyl)-5-methyl-1H-1,2,4-triazol-3-yl-thio)ethyl]azepane;
4-[3-(1-(3,4-dichlorophenyl)-5-methyl-1H-1,2,4-triazol-3-ylthio)propyl]morpholine;
1-[3-(1-(3,4-dichlorophenyl)-5-methyl-1H-1,2,4-triazol-3-yl-thio)propyl]pyrrolidine;
1-[3-(1-(3,4-dichlorophenyl)-5-methyl-1H-1,2,4-triazol-3-ylthio)propyl]-4-phenylpiperidine;
1-[4-(1-(3,4-dichlorophenyl)-5-methyl-1H-1,2,4-triazol-3-yl-thio)butyl]-4-phenylpiperidine;
4-[4-(1-(3,4-dichlorophenyl)-5-methyl-1H-1,2,4-triazol-3-yl-thio)butyl]morpholine;
1-[5-(1-(3,4-dichlorophenyl)-5-methyl-1H-1,2,4-triazol-3-ylthio)pentyl]piperidine;
4-[5-(1-(3,4-dichlorophenyl)-5-methyl-1H-1,2,4-triazol-3-ylthio)pentyl]morpholine;
1-[5-(1-(3,4-dichlorophenyl)-5-methyl-1H-1,2,4-triazol-3-ylthio)pentyl]pyrrolidine;
1-[2-(1-(3,4-dichlorophenyl)-5-methyl-1H-1,2,4-triazol-3-yl-sulfinyl)ethyl]pyrrolidine;
4-[2-(1-(3,4-dichlorophenyl)-5-methyl-1H-1,2,4-triazol-3-yl-sulfinyl)-ethyl]-morpholine;
2-[1-(3,4-dichlorophenyl)-5-methyl-1H-1,2,4-triazol-3-ylsulfinyl]-N,N-diisopropylethanamine;
1-[4-(1-(3,4-dichlorophenyl)-5-methyl-1H-1,2,4-triazol-3-ylsulfinyl)butyl]-4-phenylpiperidine;
1-{2-[1-(3,4-dichlorophenyl)-5-methyl-1H-1,2,4-triazol-3-ylsulfonyl]ethyl}pyrrolidine;
2-[1-(3,4-dichlorophenyl)-5-methyl-1H-1,2,4-triazol-3-yl-sulfonyl]-N,N-diethylethanamine;
4-[4-(1-(3,4-dichlorophenyl)-5-methyl-1H-1,2,4-triazol-3-yl-sulfonyl)-butyl]morpholine;
1-{2-[1-(3,4-dichlorophenyl)-5-methyl-1H-1,2,4-triazol-3-yloxy]ethyl}piperidine;
2-[1-(3,4-dichlorophenyl)-5-methyl-1H-1,2,4-triazol-3-yloxy]-N,N-diethylethanamine;
1-[2-(1-(3,4-dichlorophenyl)-5-methyl-1H-1,2,4-triazol-3-yloxy)ethyl]pyrrolidine;
4-[2-(1-(3,4-dichlorophenyl)-5-methyl-1H-1,2,4-triazol-3-yloxy)ethyl]morpholine;
2-(5-methyl-1-phenyl-1H-1,2,4-triazol-3-yloxy)-N,N-diethyl ethanamine;
1-[2-(5-methyl-1-phenyl-1H-1,2,4-triazol-3-yloxy)ethyl]pyrrolidine;
4-[2-(5-methyl-1-phenyl-1H-1,2,4-triazol-3-yloxy)ethyl]morpholine;
1-[2-(5-methyl-1-phenyl-1H-1,2,4-triazol-3-yloxy)ethyl]piperidine;
4-[4-(5-methyl-1-phenyl-1H-1,2,4-triazol-3-yloxy)butyl]morpholine;
1-[2-(1-(3,4-dichlorophenyl)-5-methyl-1H-1,2,4-triazol-3-ylthio)ethyl]-4-methylpiperidine;
4-[2-(5-methyl-1-phenyl-1H-1,2,4-triazol-3-ylthio)ethyl]morpholine;
4-[2-(1-(4-chlorophenyl)-5-methyl-1H-1,2,4-triazol-3-ylthio)ethyl]morpholine;
N-[2-(1-(3-chlorophenyl)-5-methyl-1H-1,2,4-triazol-3-ylthio)ethyl]-N,N-diisopropylpropan-2-amine;
1-[2-(1-(3-chlorophenyl)-5-methyl-1H-1,2,4-triazol-3-ylthio)ethyl]piperidine;
4-[2-(1-(3-chlorophenyl)-5-methyl-1H-1,2,4-triazol-3-ylthio)ethyl]morpholine;
4-[2-(1-(3-chlorophenyl)-5-methyl-1H-1,2,4-triazol-3-ylthio)ethyl]pyrrolidine;
2-[1-(3-chlorophenyl)-5-methyl-1H-1,2,4-triazol-3-ylthio]-N,N-diethylethanamine;
4-[1-(3,4-dichlorophenyl)-5-methyl-1H-1,2,4-triazol-3-ylthio]-N,N-diethylbutan-1-amine;
1-[4-(1-(3,4-dichlorophenyl)-5-methyl-1H-1,2,4-triazol-3-ylthio)butyl]piperidine;
1-[4-(1-(3,4-dichlorophenyl)-5-methyl-1H-1,2,4-triazol-3-ylthio)butyl]pyrrolidine;
2-[1-(3,4-dichlorophenyl)-5-methyl-1H-1,2,4-triazol-3-ylsulfinyl]-N,N-diethylethanamine;
1-[2-(1-(3-chlorophenyl)-5-methyl-1H-1,2,4-triazol-3-yl-sulfinyl)ethyl]pyrrolidine;
4-[2-(1-(3-chlorophenyl)-5-methyl-1H-1,2,4-triazol-3-yl-sulfinyl)ethyl]morpholine;
1-[2-(1-(3-chlorophenyl)-5-methyl-1H-1,2,4-triazol-3-yl-sulfinyl)ethyl]-N,N-diethylamine;
1-[2-(1-(3-chlorophenyl)-5-methyl-1H-1,2,4-triazol-3-yl-sulfonyl)ethyl]pyrrolidine
1-[2-(1-(3-chlorophenyl)-5-methyl-1H-1,2,4-triazol-3-yl-sulfonyl)ethyl]-N,N-diisopropilamine;
1-[2-(1-(3-chlorophenyl)-5-methyl-1H-1,2,4-triazol-3-yl-sulfonyl)ethyl]-N,N-diethylamine;

or a pharmaceutically acceptable salt, isomer, or solvate thereof.

15. The method according to claim 1 wherein the compound of formula (I) is an oxalic salt.

16. The method according to claim 1 wherein the compound of formula (I) is selected from the group consisting of:
4-{2-[1-(3,4-dichlorophenyl)-5-methyl-1H-1,2,4-triazole-3-ylthio]ethyl}morpholine oxalate;
1-{2-[1-(3,4-dichlorophenyl)-5-methyl-1H-1,2,4-triazole-3-yl-thio]ethyl}piperidine oxalate;
1-{2-[1-(3,4-dichlorophenyl)-5-methyl-1H-1,2,4-triazole-3-yl-thio]ethyl}pyrrolidine oxalate;
2-[1-(3,4-dichlorophenyl)-5-methyl-1H-1,2,4-triazole-3-yl-thio]-N,N-diisopropyl ethanamine oxalate;
2-[1-(3,4-dichlorophenyl)-5-methyl-1H-1,2,4-triazole-3-yl-thio]-N,N-diethyl ethanamine oxalate;
1-[2-(1-(3,4-dichlorophenyl)-5-methyl-1H-1,2,4-triazol-3-yl-thio)ethyl]azepane oxalate;
4-[3-(1-(3,4-dichlorophenyl)-5-methyl-1H-1,2,4-triazol-3-ylthio)propyl]morpholine oxalate;
1-[3-(1-(3,4-dichlorophenyl)-5-methyl-1H-1,2,4-triazol-3-yl-thio)propyl]pyrrolidine oxalate;
1-[3-(1-(3,4-dichlorophenyl)-5-methyl-1H-1,2,4-triazol-3-ylthio)propyl]-4-phenylpiperidine oxalate;
1-[4-(1-(3,4-dichlorophenyl)-5-methyl-1H-1,2,4-triazol-3-yl-thio)butyl]-4-phenylpiperidine oxalate;
4-[4-(1-(3,4-dichlorophenyl)-5-methyl-1H-1,2,4-triazol-3-yl-thio)butyl]morpholine oxalate;
1-[5-(1-(3,4-dichlorophenyl)-5-methyl-1H-1,2,4-triazol-3-ylthio)pentyl]piperidine oxalate;
4-[5-(1-(3,4-dichlorophenyl)-5-methyl-1H-1,2,4-triazol-3-ylthio)pentyl]morpholine oxalate;
1-[5-(1-(3,4-dichlorophenyl)-5-methyl-1H-1,2,4-triazol-3-ylthio)pentyl]pyrrolidine oxalate;
4-[2-(1-(3,4-dichlorophenyl)-5-methyl-1H-1,2,4-triazol-3-yloxy)ethyl]morpholine oxalate;
4-{2-[1-(3,4-dichlorophenyl)-5-methyl-1H-1,2,4-triazole-3-ylthio]ethyl}morpholine hydrochloride;

1-[2-(1-(3,4-dichlorophenyl)-5-methyl-1H-1,2,4-triazol-3-ylthio)ethyl]-4-methyl piperidinium oxalate;

4-[2-(5-methyl-1-phenyl-1H-1,2,4-triazol-3-ylthio)ethyl]morpholinium oxalate;

4-[2-(1-(4-chlorophenyl)-5-methyl-1H-1,2,4-triazol-3-ylthio)ethyl]morpholinium oxalate;

N-[2-(1-(3-chlorophenyl)-5-methyl-1H-1,2,4-triazol-3-ylthio)ethyl]-N,N-diisopropylpropan-2-aminium oxalate;

1-[2-(1-(3-chlorophenyl)-5-methyl-1H-1,2,4-triazol-3-ylthio)ethyl]piperidinium oxalate;

4-[2-(1-(3-chlorophenyl)-5-methyl-1H-1,2,4-triazol-3-ylthio)ethyl]morpholinium oxalate;

4-[2-(1-(3-chlorophenyl)-5-methyl-1H-1,2,4-triazol-3-ylthio)ethyl]pyrrolidinium oxalate; 2-[1-(3-chlorophenyl)-5-methyl-1H-1,2,4-triazol-3-ylthio]-N,N-diethyl-ethan aminium oxalate.

\* \* \* \* \*